United States Patent
Shtul et al.

(10) Patent No.: US 10,512,718 B2
(45) Date of Patent: Dec. 24, 2019

(54) SYSTEMS AND METHODS FOR CLEANING BODY CAVITIES

(75) Inventors: Boris Shtul, Haifa (IL); Alexey Morochovsky, Haifa (IL); Alexander Banzger, Nesher (IL); Noam Hassidov, Moshav Bustan HaGalil (IL)

(73) Assignee: Motus GI Medical Technologies Ltd., Tirat HaCarmel (IN)

( * ) Notice: Subject to any disclaimer, the term of this patent is extended or adjusted under 35 U.S.C. 154(b) by 819 days.

(21) Appl. No.: 13/557,363

(22) Filed: Jul. 25, 2012

(65) Prior Publication Data
US 2012/0289892 A1 Nov. 15, 2012

Related U.S. Application Data

(62) Division of application No. 13/521,061, filed as application No. PCT/IB2011/050121 on Jan. 11, 2011, now Pat. No. 9,895,483.
(Continued)

(51) Int. Cl.
*A61M 1/00* (2006.01)
*A61M 3/02* (2006.01)
(Continued)

(52) U.S. Cl.
CPC ........... *A61M 3/0283* (2013.01); *A61B 1/015* (2013.01); *A61B 1/31* (2013.01); *A61M 1/0023* (2013.01); *A61B 1/04* (2013.01); *A61B 1/122* (2013.01); *A61B 17/22012* (2013.01); *A61B 17/3207* (2013.01); *A61B 17/320758* (2013.01); *A61B 2217/005* (2013.01); *A61B 2217/007* (2013.01); *A61F 5/442* (2013.01); *A61F 5/445* (2013.01); *A61M 1/006* (2014.02); *A61M 1/008* (2013.01); *A61M 1/0035* (2014.02); *A61M 1/0084* (2013.01); *A61M 3/0275* (2013.01);
(Continued)

(58) Field of Classification Search
CPC .............. A61M 3/0283; A61M 1/0023; A61M 2210/10664; A61B 1/015; A61B 1/31; A61B 1/04
USPC ........................................................ 604/317
See application file for complete search history.

(56) References Cited

U.S. PATENT DOCUMENTS

3,735,751 A 5/1973 Katz
4,117,847 A 10/1978 Clayton
(Continued)

FOREIGN PATENT DOCUMENTS

AU 2005203844 7/2005
CN 1120805 4/1996
(Continued)

OTHER PUBLICATIONS

International Preliminary Report on Patentability dated Dec. 27, 2012 From the International Bureau of WIPO Re. Application No. PCT/IL2011/000470.
(Continued)

*Primary Examiner* — Andrew J Mensh

(57) ABSTRACT

Systems and methods for cleaning body cavities are presented. Some embodiments reduce size of fecal matter pieces within an evacuation conduit. Some comprise devices and methods for purging an evacuation conduit. Some comprise reduced cross-sectional profiles of a cleaning device. Some protect intestinal tissue by preventing exposure to excessively high and low pressures.

23 Claims, 14 Drawing Sheets

Related U.S. Application Data

(60) Provisional application No. 61/293,758, filed on Jan. 11, 2010, provisional application No. 61/354,226, filed on Jun. 13, 2010.

(51) Int. Cl.

| | |
|---|---|
| *A61B 1/015* | (2006.01) |
| *A61B 1/31* | (2006.01) |
| *A61F 5/445* | (2006.01) |
| *A61M 16/04* | (2006.01) |
| *A61F 5/442* | (2006.01) |
| *A61B 17/3207* | (2006.01) |
| *A61M 25/00* | (2006.01) |
| *B08B 9/045* | (2006.01) |
| *A61B 1/12* | (2006.01) |
| *A61B 17/22* | (2006.01) |
| *B08B 9/043* | (2006.01) |
| *A61B 1/04* | (2006.01) |

(52) U.S. Cl.
CPC ....... *A61M 3/0295* (2013.01); *A61M 16/0463* (2013.01); *A61M 2025/0019* (2013.01); *A61M 2025/0025* (2013.01); *A61M 2205/3334* (2013.01); *A61M 2205/3389* (2013.01); *A61M 2210/1064* (2013.01); *B08B 9/045* (2013.01); *B08B 9/0436* (2013.01)

(56) References Cited

U.S. PATENT DOCUMENTS

| | | | |
|---|---|---|---|
| 4,257,422 A | 3/1981 | Duncan | |
| 4,445,509 A | 5/1984 | Auth | |
| 4,596,554 A | 6/1986 | Dastgeer | |
| 4,682,979 A | 7/1987 | Girouard | |
| 4,857,046 A | 8/1989 | Stevens et al. | |
| 4,874,363 A | 10/1989 | Abell | |
| 4,893,634 A | 1/1990 | Kulik et al. | |
| 4,902,276 A * | 2/1990 | Zakko | A61B 17/22 604/28 |
| 5,019,056 A | 5/1991 | Lee et al. | |
| 5,047,040 A | 9/1991 | Simpson et al. | |
| 5,350,369 A | 9/1994 | Workman et al. | |
| 5,443,445 A | 8/1995 | Peters et al. | |
| 5,542,929 A * | 8/1996 | Laabs | A61M 1/0047 604/119 |
| 5,630,795 A | 5/1997 | Kuramoto et al. | |
| 5,782,747 A | 7/1998 | Zimmon | |
| 5,788,650 A | 8/1998 | Dotolo | |
| 6,149,581 A * | 11/2000 | Klingenstein | A61B 6/481 600/114 |
| 6,500,142 B1 | 12/2002 | Harreld et al. | |
| 6,595,971 B1 | 7/2003 | Von Dyck et al. | |
| 6,984,226 B1 | 1/2006 | Abell et al. | |
| 8,065,772 B2 | 11/2011 | Maguire, Jr. et al. | |
| 8,075,539 B2 | 12/2011 | Nishtala et al. | |
| 2002/0045852 A1 | 4/2002 | Saab | |
| 2003/0176833 A1 | 9/2003 | Libermann | |
| 2005/0004533 A1 | 1/2005 | Smith | |
| 2005/0054996 A1 | 3/2005 | Gregory | |
| 2005/0070933 A1 | 3/2005 | Leiboff | |
| 2005/0085694 A1 | 4/2005 | Nakao | |
| 2005/0096503 A1 | 5/2005 | Conteas | |
| 2005/0119628 A1 | 6/2005 | Sant et al. | |
| 2005/0148954 A1 | 7/2005 | Abell | |
| 2005/0261553 A1 | 11/2005 | Swain et al. | |
| 2006/0025728 A1 | 2/2006 | Leiboff et al. | |
| 2006/0025729 A1 | 2/2006 | Leiboff et al. | |
| 2006/0173244 A1 | 8/2006 | Boulais et al. | |
| 2007/0015965 A1 * | 1/2007 | Cox | A61B 1/00082 600/114 |
| 2007/0078444 A1 * | 4/2007 | Larsson | A61M 1/0031 604/540 |
| 2008/0167606 A1 | 7/2008 | Dann et al. | |
| 2008/0255596 A1 | 10/2008 | Jenson et al. | |
| 2008/0262308 A1 | 10/2008 | Prestezog et al. | |
| 2009/0143722 A1 | 6/2009 | Kim | |
| 2009/0264910 A1 | 10/2009 | Laufer | |
| 2010/0256447 A1 * | 10/2010 | Dubi | A61B 1/00082 600/115 |
| 2011/0160657 A1 | 6/2011 | Gobel | |
| 2012/0253284 A1 | 10/2012 | Nitsan et al. | |
| 2012/0289910 A1 | 11/2012 | Shtul et al. | |
| 2013/0066297 A1 | 3/2013 | Shtul et al. | |
| 2013/0085442 A1 | 4/2013 | Shtul et al. | |
| 2013/0296771 A1 | 11/2013 | Shtul et al. | |

FOREIGN PATENT DOCUMENTS

| | | | |
|---|---|---|---|
| CN | 1868554 | 11/2006 | |
| CN | 101607100 | 12/2009 | |
| DE | 8904403 | 7/1989 | |
| EP | 1262205 | 12/2002 | |
| EP | 2529779 | 12/2012 | |
| JP | 02-191464 | 7/1990 | |
| JP | 05-161711 | 6/1993 | |
| JP | 2003-010324 | 1/2003 | |
| WO | WO 88/00840 | 2/1988 | |
| WO | WO 92/17219 | 10/1992 | |
| WO | WO 94/18894 | 9/1994 | |
| WO | WO 99/60934 | 12/1999 | |
| WO | WO 2006/039511 | 4/2006 | |
| WO | WO 2006/086826 | 8/2006 | |
| WO | WO 2008/093288 | 8/2008 | |
| WO | WO 2009/125387 | 10/2009 | |
| WO | WO 2009125387 A2 * | 10/2009 | ....... A61B 17/32037 |
| WO | WO 2009/143201 | 11/2009 | |
| WO | WO 2011/083450 | 7/2011 | |
| WO | WO 2011/083451 | 7/2011 | |
| WO | WO 2011/158232 | 12/2011 | |

OTHER PUBLICATIONS

Official Action dated Nov. 6, 2013 From the US Patent and Trademark Office Re. U.S. Appl. No. 13/557,371.
Office Action and Search Report dated Jan. 17, 2014 From the State Intellectual Property Office of the People's Republic of China Re. Application No. 201180013505.6 and Its Summary in English.
Notification of Office Action dated Apr. 2, 2014 From the State Intellectual Property Office of the People's Republic of China Re. Application No. 201180039602.2 and Its Translation Into English.
Official Action dated May 21, 2014 From the US Patent and Trademark Office Re. U.S. Appl. No. 13/521,061.
Official Action dated Jul. 2, 2014 From the US Patent and Trademark Office Re. U.S. Appl. No. 13/557,371.
Examination Report dated Jul. 17, 2014 From the Instituto Mexicano de la Propiedad Industrial Re. Application No. MX/a/2012/008056 and Its Translation Into English.
Office Action and Search Report dated Oct. 10, 2014 From the State Intellectual Property Office of the People's Republic of China Re. Application No. 201180013505.6 and Its Translation Into English.
Applicant-Initiated Interview Summary dated Nov. 14, 2014 From the US Patent and Trademark Office Re. U.S. Appl. No. 13/557,371.
Notice of Reason for Rejection dated Nov. 7, 2014 From the Japanese Patent Office Re. Application No. 2012-548515 and Its Translation Into English.
Notification of Office Action and Search Report dated Nov. 24, 2014 From the State Intellectual Property Office of the People's Republic of China Re. Application No. 201180039602.2.
Official Action dated Dec. 15, 2014 From the US Patent and Trademark Office Re. U.S. Appl. No. 13/521,061.
Translation Dated Dec. 10, 2014 of Notification of Office Action and Search Report dated Nov. 24, 2014 From the State Intellectual Property Office of the People's Republic of China Re. Application No. 201180039602.2.
Applicant-Initiated Interview Summary dated Mar. 20, 2015 From the US Patent and Trademark Office Re. U.S. Appl. No. 13/521,061.

(56) References Cited

OTHER PUBLICATIONS

Notice of Reason for Rejection dated Mar. 20, 2015 From the Japanese Patent Office Re. Application No. 2013-514838 and Its Translation Into English.
Restriction Official Action dated Jun. 26, 2015 From the US Patent and Trademark Office Re. U.S. Appl. No. 13/703,986.
Official Action dated Sep. 15, 2015 From the US Patent and Trademark Office Re. U.S. Appl. No. 13/557,371.
Restriction Official Action dated Nov. 23, 2015 From the US Patent and Trademark Office Re. U.S. Appl. No. 13/521,483.
Official Decision of Rejection dated Feb. 2, 2016 From the Japanese Patent Office Re. Application No. 2013-514838 and Its Translation Into English.
Official Action dated Mar. 24, 2016 From the US Patent and Trademark Office Re. U.S. Appl. No. 13/521,061.
Official Action dated Mar. 24, 2016 From the US Patent and Trademark Office Re. U.S. Appl. No. 13/557,371.
Official Action dated Apr. 15, 2016 From the US Patent and Trademark Office Re. U.S. Appl. No. 13/521,483.
International Preliminary Report on Patentability dated Jul. 26, 2012 From the International Bureau of WIPO Re. Application No. PCT/IB2011/050121.
International Preliminary Report on Patentability dated Jul. 26, 2012 From the International Bureau of WIPO Re. Application No. PCT/IB2011/050120.
Communication Relating to the Results of the Partial International Search dated Jun. 6, 2011 From the International Searching Authority Re. Application No. PCT/IB2011/050121.
Communication Relating to the Results of the Partial International Search dated Nov. 15, 2011 From the International Searching Authority Re. Application No. PCT/IL2011/000470.
International Search Report and the Written Opinion dated Feb. 17, 2012 From the International Searching Authority Re. Application No. PCT/IB2011/000470.
International Search Report and the Written Opinion dated Aug. 18, 2011 From the International Searching Authority Re. Application No. PCT/IB2011/050121.
International Search Report and the Written Opinion dated Aug. 26, 2011 From the International Searching Authority Re: Application No. PCT/IB 11/50120.
Invitation to Pay Additional Fees dated Jun. 22, 2011 From the International Searching Authority Re. Application No. PCT/IB2011/50120.
Communication Pursuant to Article 94(3) EPC dated Jul. 5, 2016 From the European Patent Office Re. Application No. 11703037.9.
Communication Pursuant to Article 94(3) EPC dated Jul. 12, 2016 From the European Patent Office Re. Application No. 11732520.9.
Official Action dated Oct. 17, 2016 From the US Patent and Trademark Office Re. U.S. Appl. No. 13/521,483.
Applicant-Initiated Interview Summary dated Nov. 7, 2016 From the US Patent and Trademark Office Re. U.S. Appl. No. 13/703,986. (3 pages).
Official Action dated Jun. 23, 2016 From the US Patent and Trademark Office Re. U.S. Appl. No. 13/703,986.
Official Action dated Jun. 29, 2017 From the US Patent and Trademark Office Re. U.S. Appl. No. 13/557,371. (34 pages).
Applicant-Initiated Interview Summary dated Apr. 13, 2017 From the US Patent and Trademark Office Re. U.S. Appl. No. 13/703,986. (3 pages).

Notice of Reason for Rejection dated Mar. 31, 2017 From the Japan Patent Office Re. Application No. 2016-110785 and Its Translation Into English. (8 Pages).
Supplementary European Search Report and the European Search Opinion dated Mar. 29, 2017 From the European Patent Office Re. Application No. 11731727.1. (9 Pages).
Advisory Action Before the Filing of an Appeal Brief dated Jan. 6, 2017 From the US Patent and Trademark Office Re. U.S. Appl. No. 13/521,483. (4 pages).
Applicant-Initiated Interview Summary dated Dec. 2, 2016 From the US Patent and Trademark Office Re. U.S. Appl. No. 13/521,483. (3 pages).
Applicant-Initiated Interview Summary dated Feb. 16, 2017 From the US Patent and Trademark Office Re. U.S. Appl. No. 13/557,371. (4 pages).
Official Action dated Feb. 13, 2017 From the US Patent and Trademark Office Re. U.S. Appl. No. 13/703,986. (31 pages).
Official Action dated Jan. 17, 2017 From the US Patent and Trademark Office Re. U.S. Appl. No. 13/557,371. (34 pages).
Official Action dated Dec. 30, 2016 From the US Patent and Trademark Office Re. U.S. Appl. No. 13/521,061. (31 pages).
Official Action dated Aug. 24, 2017 From the US Patent and Trademark Office Re. U.S. Appl. No. 13/703,986. (18 pages).
Notice of Reason for Rejection dated Dec. 1, 2017 From the Japan Patent Office Re. Application No. 2016-110785 and Its Translation Into English. (11 Pages).
Notice of Reason for Rejection dated Mar. 23, 2018 From the Japan Patent Office Re. Application No. 2016-110785 and Its Translation Into English. (4 Pages).
Official Action dated Jun. 21, 2018 From the US Patent and Trademark Office Re. U.S. Appl. No. 13/521,483. (16 pages).
Advisory Action Before the Filing of an Appeal Brief dated Feb. 22, 2018 From the US Patent and Trademark Office Re. U.S. Appl. No. 13/703,986. (3 pages).
Official Action dated Oct. 26, 2017 From the US Patent and Trademark Office Re. U.S. Appl. No. 13/521,483. (38 pages).
Applicant-Initiated Interview Summary dated Aug. 29, 2018 From the US Patent and Trademark Office Re. U.S. Appl. No. 13/521,483. (3 pages).
Communication Pursuant to Article 94(3) EPC dated Sep. 25, 2018 From the European Patent Office Re. Application No. 11731727.1. (6 Pages).
Official Action dated Sep. 5, 2018 From the US Patent and Trademark Office Re. U.S. Appl. No. 13/703,986. (38 pages).
Official Action dated May 15, 2019 From the US Patent and Trademark Office Re. U.S. Appl. No. 13/703,986. (17 pages).
Applicant-Initiated Interview Summary dated Jun. 19, 2019 From the US Patent and Trademark Office Re. U.S. Appl. No. 13/703,986. (7pages).
Examination Report Under Sections 12 & 13 of the Patents Act, 1970 and the Patents Rules, 2003 dated Jun. 21, 2019 From the Government of India, Intellectual Property India, Patents, Designs, Trade Marks, Geographical Indications Re. Application No. 1700/MUMNP/2012. (5 Pages).
Official Action dated Dec. 30, 2015 From the US Patent and Trademark Office Re. U.S. Appl. No. 13/703,986.
Restriction Official Action dated Dec. 19, 2013 From the US Patent and Trademark Office Re. U.S. Appl. No. 13/521,061.

\* cited by examiner

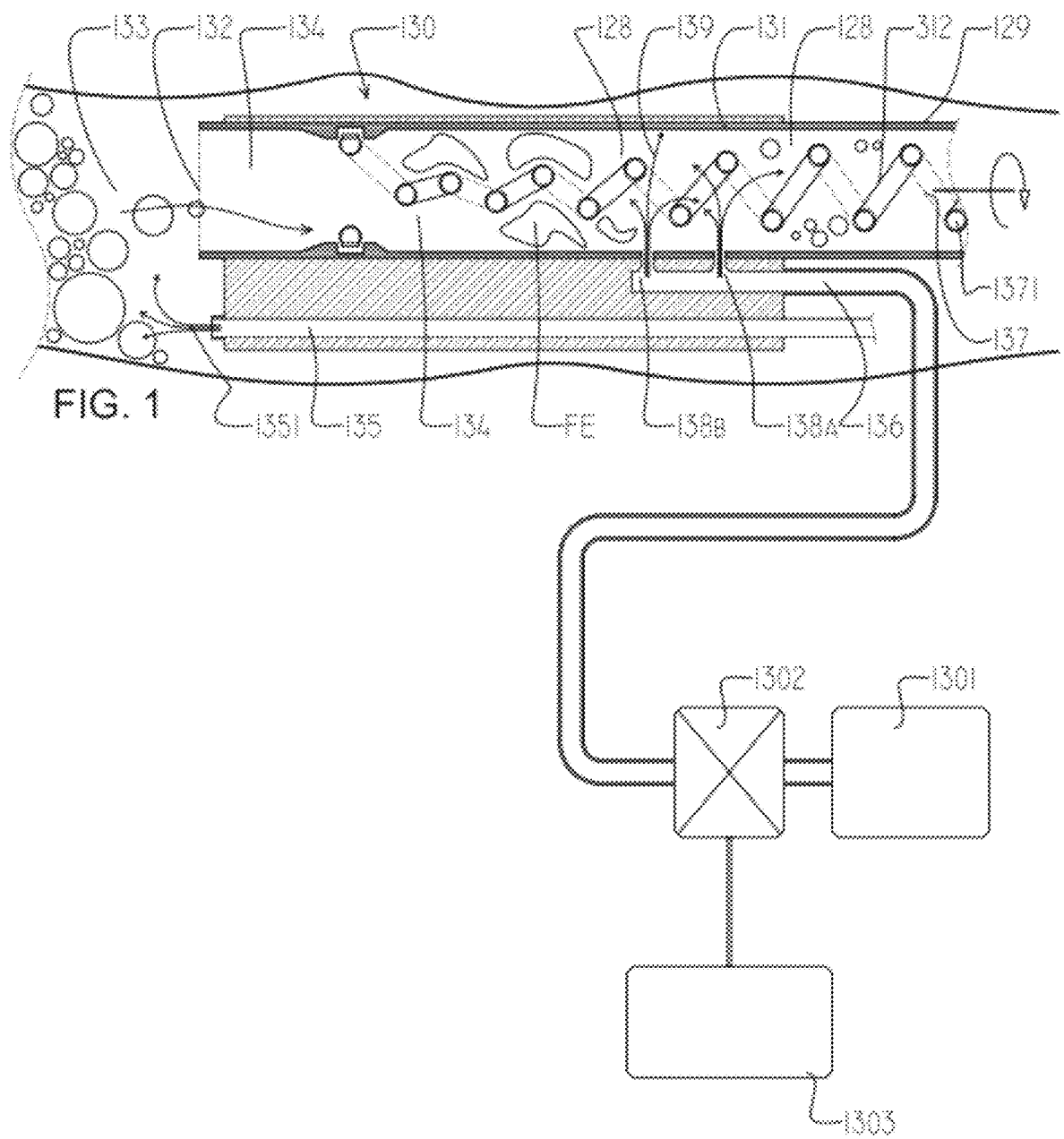

SYSTEMS AND METHODS FOR CLEANING BODY CAVITIES

RELATED APPLICATIONS

This application is a Divisional of U.S. patent application Ser. No. 13/521,061 filed on Jul. 9, 2012, which is a National Phase of PCT Application No. PCT/IB2011/050121 having International filing date of Jan. 11, 2011, which claims the benefit of priority under 35 USC § 119(e) of U.S. Provisional Patent Application Nos. 61/293,758 filed on Jan. 11, 2010 and 61/354,226 filed on Jun. 13, 2010. PCT Application No. PCT/IB2011/050121 was co-filed with PCT Application No. PCT/IB2011/050120 having International filing date of Jan. 11, 2011. The contents of the above applications are all incorporated by reference as if fully set forth herein in their entirety.

FIELD AND BACKGROUND OF THE INVENTION

The present invention, in some embodiments thereof, relates to systems for cleaning body conduits and/or body cavities, and more particularly, but not exclusively, to systems for cleaning the lower GI tract.

The well-known enema has a long history as a system for cleaning the colon. An enema is a tube inserted into the lower colon through the rectum, and used to inject water or other liquids into the colon. Cleaning is achieved when the injected liquid, mixed with fecal matter, is ejected from the body by natural processes.

More recently, closed hydrotherapy (or cleansing) systems have been introduced, wherein a liquid source tube, capable of supplying liquid under low pressure, is paired with an evacuation tube In a first phase of the cleansing cycle liquids flow from the rectum up the colon due to the low pressure and fill the colon cavity, mixing with feces and partially dissolving it; in a second phase of the cleansing cycle the mixtures of liquid and fecal matter can then be evacuated from the bowel through the evacuation tube. In similarity to the enema, the speculum of such systems is usually introduced approximately 6-8 centimeters into the body. An example is shown at wwwdotdotoloresearchdotcom.

A colonoscope (a hand-driven flexible endoscope able to reach further into the lower GI system, up to the cecum) has been suggested for use in cleaning of the GI tract. However, because of the size limitations of working channels of endoscopes the throughput of the colonoscope when used for cleaning is not great, and would be appropriate at most for cleaning local feces spots. The colonoscope is not effective for cleaning a lower GI system which may be filled with up to 2 liters of feces distributed over a lumen more than 1.5 meters long.

Easy-glide, at wwwdoteasy-glidedotcom, advertises a system which connects to an endoscope and which sprays water into an intestine through an irrigation channel and which withdraws matter from the intestine by providing suction through an exhaust channel connected to a by standard medical vacuum line.

SUMMARY OF THE INVENTION

The present invention, in some embodiments thereof, relates to system for cleaning body cavities and for transporting material in and out of body cavities. Embodiments presented herein facilitate evacuation of materials cleaned from body conduits, and provide safety features which prevent damage to body tissues during cleaning.

As used herein, the term "cleaning device" relates to devices for cleaning a colon or other portion of an intestine. A "cleaning device" may be an independent device, a device attachable to an endoscope or colonoscope, or a part of an endoscope or colonoscope.

Many cleaning devices comprise an evacuation conduit through which matter may be removed from the intestine and transported out of the body. The turns "evacuation conduit", "exhaust conduit", "exhaust lumen", "evacuation lumen", "evacuation channel" and "exhaust channel" are used interchangeably in this document. All refer to a conduit/lumen/channel through which matter may be removed from the intestine and transported out of the body.

Cleaning devices currently known in the art supply liquid into a colon to mix with, dilute, and partially dissolve fecal matter, so that the resultant mixture of liquid and fecal matter can be evacuated through an exhaust conduit such as a flexible tube.

A potential advantage of some embodiments of the invention is dealing with the large chunks of fecal matter that sometimes result, and/or with or with undissolvable components of fecal matter, such as undigested food parts (e.g. corn seeds). These tend to impede throughput of the exhaust conduits by clogging up entrances to the conduits or the conduits themselves, leading to reduced throughput and longer operation time, and sometimes preventing use of a cleaning device.

Some embodiments presented herein, in some aspects thereof, provide systems and methods for "graining" the fecal matter within an exhaust conduit. (The term "graining" as used herein refers to reducing breaking, shredding, cutting, or otherwise reducing large pieces of such matter to small pieces which combine into a slurry which can be transported through an exhaust conduit and will have a reduced tendency to block or clog the conduit.) These included methods and devices for cutting and shredding fecal matter using high-velocity liquid sprays within an exhaust conduit, and methods and devices for shredding matter within an exhaust conduit by grinding the matter, by subjecting it to turbulence, and by pulling it apart by subjecting it contradictory pulling forces.

Some embodiments presented herein, in some aspects thereof, comprise devices and methods for purging an evacuation conduit. Such purging can be in addition to or instead of evacuation.

Some embodiments presented herein, in some aspects thereof, comprise mechanisms for delivering mechanical power to mechanical shredding devices within an exhaust conduit.

Some embodiments presented herein, in some aspects thereof, comprise design features which reduce cross-sectional profile of a cleaning device.

Some embodiments presented herein, in some aspects thereof, protect intestinal tissue by preventing contact between intestinal tissue and moving parts of a cleaning device, by preventing exposure of tissue to excessive pressure due to over-inflation of the intestine, by aiming potentially dangerous jets of water at an artificial element (such as inside a tube), rather than at a portion of the body and/or by preventing exposure of tissue to dangerously low pressure due to suction in a exhaust conduit.

In exemplary embodiments of the invention, features of various of the embodiments are combined to provide features from two or more of the above classes.

In an exemplary embodiment of the invention, for the colon, the outer diameter of a system is between 0.5 and 4 cm, for example, between 1 and 2.5 cm. In an exemplary embodiment of the invention, the length of a tube inserted into the colon is between 0.5 and 4 meters, for example, between 1 and 2.5 meters. Optionally, apertures are sized for receiving fecal pieces of diameter between 0.2 and 3 cm, for example, between 0.5 and 2 cm in diameter. Optionally, apertures are sized less than 4 cm, or less than 3 or 2 or 1 cm or intermediate sizes, to reduce the possibility and extent of intestinal protrusion therethrough. Optionally, moving parts are located, for example, 1 cm, 2 cm, 3 cm or more or intermediate distances from apertures.

There is provided in accordance with an exemplary embodiment of the invention, a cleaning device insertable in a colon and which comprises an evacuation conduit for transporting material from said colon out of a body, and which comprises
  a) a closure mechanism positioned near a distal end of said evacuation conduit and which opened allows matter from said intestine to flow into said evacuation conduit, and which closed at least partially prevents fluid in said evacuation conduit from flowing through said distal end of said evacuation conduit and into said intestine. Optionally, the device comprises
  b) a fluid supply conduit having a proximal connection to a fluid supply and at least one distal orifice within said evacuation conduit.

Alternatively or additionally, the device comprises
  c) a vacuum source connectable to a distal end of said evacuation conduit.

There is provided in accordance with an exemplary embodiment of the invention, a method for cleaning a colon, comprising:
  a) introducing a liquid into a colon;
  b) providing an evacuation conduit for evacuating material from said colon; and
  c) occasionally closing a closure mechanism positioned near a distal end of said evacuation conduit, said closure mechanism when closed at least partially prevents fluid in said evacuation conduit from flowing through a distal end of said evacuation conduit, and
  d) while said closure mechanism is closed, inducing a pressure differential between a medial portion of said conduit and a proximal end of said conduit, thereby purging said conduit. Optionally the method comprises inducing said pressure differential by supplying a fluid into said conduit at a position which is proximal to said closure mechanism, said fluid being supplied while said closure mechanism is closed. Optionally or alternatively, the method comprises inducing said pressure differential by attaching a proximal end of said evacuation conduit to a vacuum source while said closure mechanism is closed. Optionally said closure mechanism is closed mechanically.

In an exemplary embodiment of the invention, said closure mechanism is closed by hydraulic pressure.

In an exemplary embodiment of the invention, said closure mechanism is a one-way valve.

There is provided in accordance with an exemplary embodiment of the invention, a method for cleaning a colon by drawing fecal matter from a colon in an evacuation conduit, the method comprises
  a) inserting in a colon a cleaning device which comprises an evacuation conduit;
  b) irrigating the colon to liberate fecal material;
  c) drawing liberated fecal material into said evacuation conduit;
  d) directing a high-velocity fluid jet at said drawn fecal matter, such that on an opposite side of said fecal matter is a portion of the evacuation conduit; and
    reducing said drawn fecal matter in size by said jet thereby facilitating drawing said fecal matter from said colon through said conduit.

There is provided in accordance with an exemplary embodiment of the invention, a cleaning device which comprises
  a) a tube insertable in a colon and having a lumen;
  b) a first helical device positioned within said lumen;
  c) a second helical device positioned within said lumen; and
  d) a mechanism for rotating said first and second helical devices in tandem. Optionally, said first and second helical devices have windings spaced at least 0.5 mm apart. Optionally or alternatively, said second helical device is positioned within said first helical device and is substantially coaxial with it. Optionally or alternatively, said first helical device is attached to said tube. Optionally or alternatively, said tube has a smooth exterior surface and an abrasive interior surface. Optionally or alternatively, said second helical device is positioned to the size of said first helical device. Optionally or alternatively, said second helical device is configured to rotate in an opposite direction from said first helical device.

There is provided in accordance with an exemplary embodiment of the invention, a cleaning device that comprises
  a) an evacuation conduit which comprises a plurality of lobes running side by side and in fluid communication with each other along at least a portion of the length of the lumen; and
  b) at least one rotatable device housed in one of said lobes and free to rotate within said lobe, but prevented by shape of said lobe from moving laterally into another of said plurality of lobes. Optionally, the device comprises a rotatable device in each of two lobes. Optionally, said two rotatable devices have a helical form, and when positioned each in its lobe, said helices overlap. Optionally or alternatively, said rotatable device is a helical device.

In an exemplary embodiment of the invention, said rotatable devices is a brush. Optionally, said brush comprises bristles long enough to extend from a lobe in which said brush is positioned into another of said lobes.

In an exemplary embodiment of the invention, said two rotatable devices rotate independently. Optionally, at least one of said rotatable devices is free to advance and retract within said lobe of said lumen.

In an exemplary embodiment of the invention, said rotatable device comprises a paddle.

There is provided in accordance with an exemplary embodiment of the invention, a cleaning device a cleaning device which comprises an evacuation conduit which contains a tool which comprises
  a) a distal operational portion designed to interact with material within said conduit, and
  b) a medial portion which transfers rotational power from a proximal energy source to distal portion.

There is provided in accordance with an exemplary embodiment of the invention, a cleaning device insertable in an intestine which comprises a) an evacuation conduit which comprises a matter transportation mechanism and sized to be placed in an intestine;
b) a fluid input nozzle positioned to supply water to said intestine when said device is inserted therein;
c) a pressure sensor positioned to measure pressure within said intestine when said device is inserted therein; and
d) a controller configured to respond when said sensor reports a pressure above a preset amount, said response comprising at least one of:
   (i) ceasing or reducing supply of water through said nozzle;
   (ii) increasing an evacuation rate; and
   (iii) purging said evacuation conduit.

There is provided in accordance with an exemplary embodiment of the invention, a cleaning device which comprises
a) a tube insertable in a colon and having a lumen, an outer wall of said tube being smooth and an inner wall of said tube being rough;
b) helical device positioned within said lumen and having windings spaced at least 0.5 mm apart; and
c) a mechanism for rotating said helical device.

There is provided in accordance with an exemplary embodiment of the invention, a cleaning device for cleaning an intestine which comprises
a) a conduit for delivering a fluid to said intestine;
b) a pressure sensor operable to measure ambient pressure in said intestine; and
c) a controller configured to control delivery of fluid through said fluid delivery conduit as a function of measured intra-intestinal pressure measured by said sensor.

There is provided in accordance with an exemplary embodiment of the invention, a cleaning device which comprises
a) an evacuation conduit which comprises a matter transport mechanism;
b) a pressure sensor positioned within said conduit; and
c) a controller configured control said matter transport mechanism as a function of a measured pressure reported by said sensor.

There is provided in accordance with an exemplary embodiment of the invention, a cleaning device insertable in an intestine having an evacuation conduit which comprises a first distal opening and a matter transportation mechanism, characterized in that said conduit further comprises additional openings by which fluid from within said intestine may enter said conduit when drawn therein by a vacuum within said conduit. Optionally, the device comprises a fluid source for providing a fluid to at least one of said additional openings. Optionally or alternatively, at least some of said additional openings are lateral openings to said conduit. Optionally or alternatively, said fluid source is positioned to provide a fluid which washes at least one of said additional openings.

There is provided in accordance with an exemplary embodiment of the invention, a cleaning device which comprises an exhaust lumen which comprises a hollow central pipe connected to a fluid source, a helical device mounted on said pipe, and a motor for rotating said helical device by rotating said central pipe. Optionally, said central pipe comprises openings through which a fluid is provided if pressure within said exhaust lumen drops below a preset value.

There is provided in accordance with an exemplary embodiment of the invention, a cleaning device which comprises an exhaust lumen and a dedicated fluid supply channel used to provide fluid flow into said exhaust lumen when pressure within said lumen drops below a predetermined value.

There is provided in accordance with an exemplary embodiment of the invention, apparatus for fecal decomposition, comprising:
an evacuation conduit sized for insertion into a colon;
a source of a high velocity jet aimed at a wall of said conduit.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein may be performed by a "controller", which may comprise a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1 presents a cleaning device which comprises a high-pressure fluid input for shredding matter within an exhaust lumen of the device, according to some embodiments of the present invention;

FIG. 8B presents a bypass orifice according to an embodiment of the present invention; FIG. 8A presents a similar configuration without the bypass;

FIGS. 10B-10D also comprise an internal bypass.

DESCRIPTION OF SPECIFIC EMBODIMENTS OF THE INVENTION

Figure 2A:
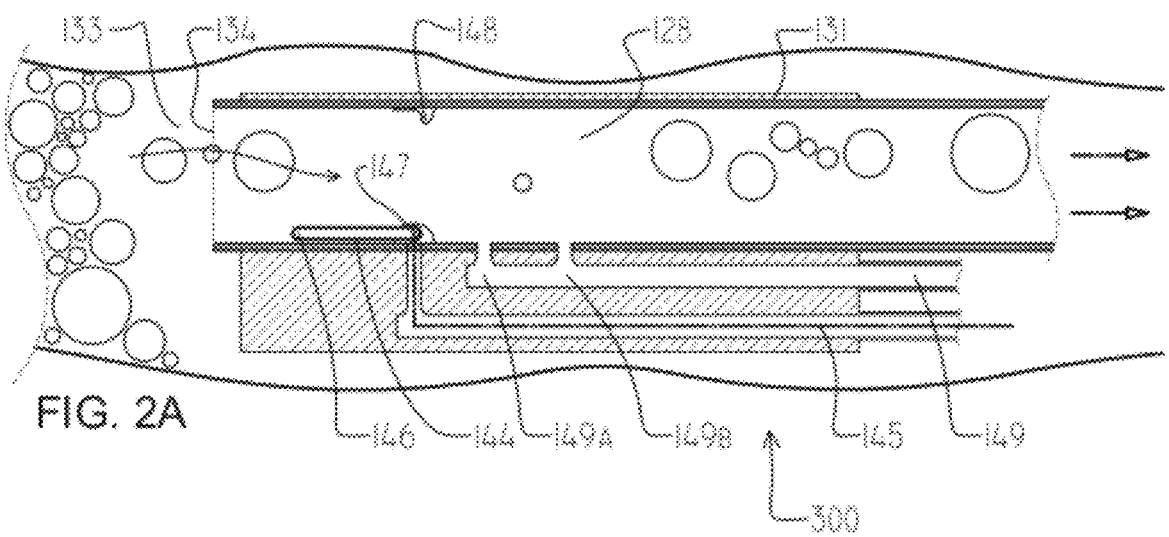
FIGS. 2A-2F present cleaning devices which comprise mechanism for purging an exhaust passageway, according to some embodiments of the present invention.

The present invention, in some embodiments thereof, relates to a system for cleaning body conduits and/or body cavities, and more particularly, but not exclusively, to a system for cleaning the lower GI tract.

It is to be noted that features from the various embodiments presented and discussed herein can be mixed and combined. The figures and discussion of the figures have been selected to simplify presentation and understanding in isolation of features which are intended to be used together. Note also that where specific utilizations of presented features are mentioned, these utilizations are exemplary only and should not be considered limiting; the described embodiments illustrate features which may be used to answer a variety of needs and purposes including, but not limited to, purposes mentioned in this disclosure.

Embodiments are presented below in the following general order:
Embodiments illustrating features that can be suitable for purging an evacuation conduit of a cleaning device (FIGS. 2A-2F)
Embodiments illustrating features that can be suitable for 'graining' of fecal matter within an evacuation conduit of a cleaning device by one or more of:
Cutting and shredding fecal matter using high-velocity liquid sprays, (FIG. 1)
Grinding within an evacuation conduit (FIGS. 5A-6B)
Creating turbulence within an evacuation conduit (FIGS. 4A-4F)
Pulling matter pieces apart by subjecting them to contradictory pulling forces (FIGS. 4A-4F)
Embodiments illustrating features that can be suitable for providing mechanical power to graining tools within an evacuation conduit (FIG. 6B)
Embodiments illustrating features that can be suitable for reducing the cross-sectional profile of a cleaning device (FIGS. 3A-3C), and
Embodiments illustrating features that can be suitable for protecting intestinal tissue by one or more of
Preventing exposure of tissue to excessive pressure due to over-inflation of an intestine when liquid is supplied for cleaning purposes, and
Preventing exposure of tissue to dangerously low pressure when suction is created in an evacuation conduit.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Cleaning Device which Comprises a Purging System

Attention is now drawn to FIGS. 2A-2F which illustrate an endoscope or other cleaning device 300 with a self purging system, according to some embodiments of the present invention.

FIGS. 2A-2F present a cleaning device 300 insertable in a colon 133 and which comprises an evacuation conduit 128 (also called an "exhaust lumen 128" herein) for transporting material from said colon out of a body. Conduit 128 comprises a closure mechanism 144 positioned near a distal end 134 of conduit 128. Closure mechanism 144 may be a rotatable flap 146 rotating on a hinge 147, or may be a one-way valve operated hydraulically, or may be any other closure mechanism.

When closure mechanism 144 is open, matter from intestine 133 can flow into conduit 128 and be moved out of the body. When closure mechanism 144 is closed, it at least partially (and in some embodiments entirely) prevents fluid from conduit 128 from flowing through distal end 134 and into intestine 133. When closure mechanism 144 is closed, it partially or substantially or completely prevents fluid movement within conduit 128 from influencing tissues of intestine 133.

Figure 2B:
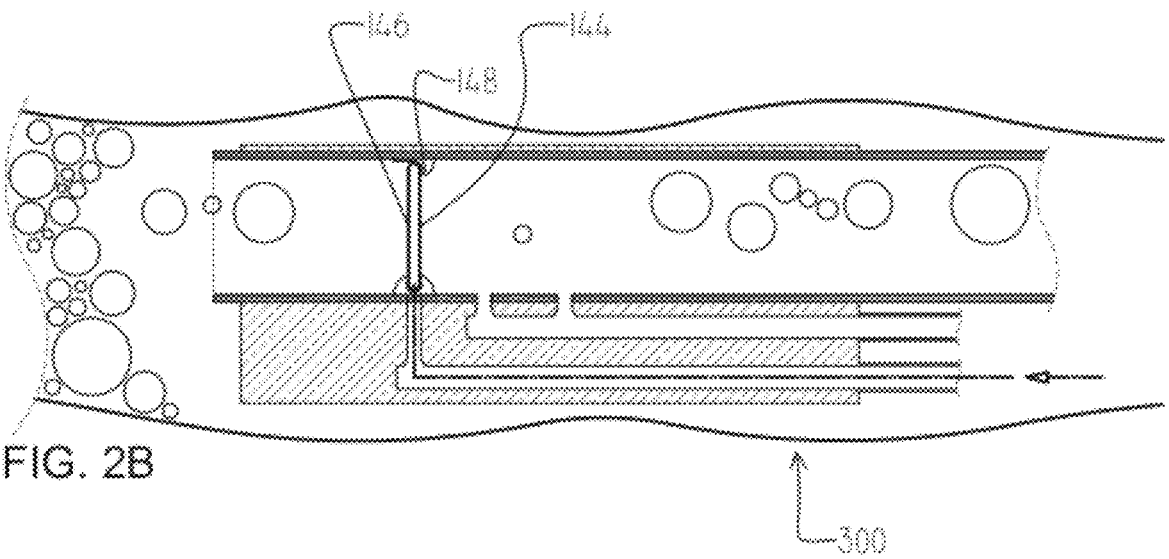
Figure 2C:
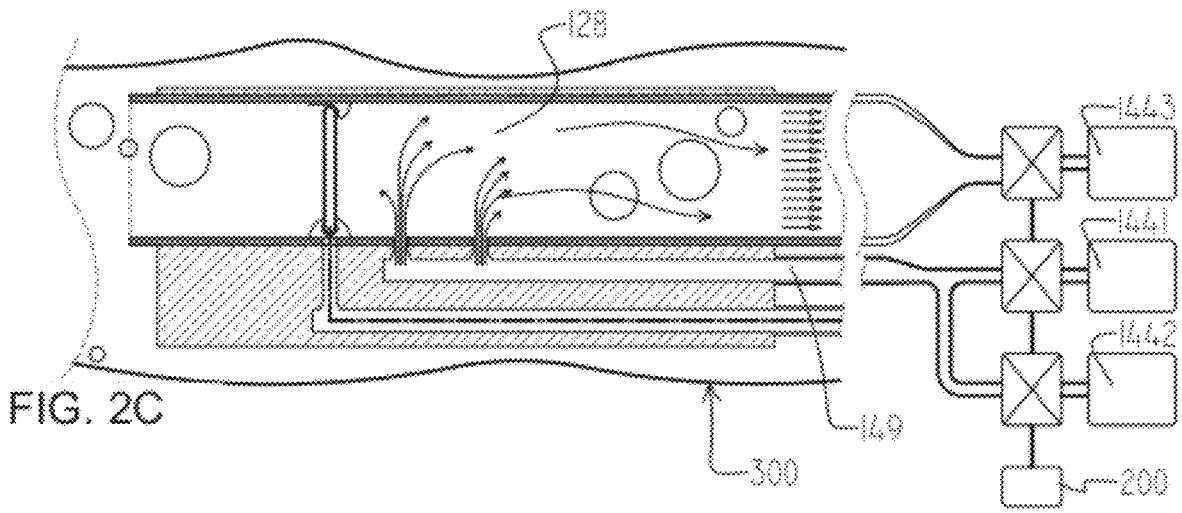

Cleaner 300 may comprise a high-pressure fluid source 1441 and/or a high-volume fluid source 1442 and/or a vacuum source 1443, optionally commanded by values which are optionally controlled by a controller 200, as shown in FIG. 2C.

Fluid sources 1441 and 1442, if present, connect to a fluid input channel 149 having distal orifices 149A and 149B. These orifices conduct fluid in channel 149 to enter conduit 128 at a position proximal to closure mechanism 144 and optionally near to mechanism 144.

Cleaner 300 may also comprise a vacuum source 1443, also optionally controlled by a valve commanded by controller 200.

According to some methods of using cleaner 300, cleaner 300 can be used to introduce a cleaning liquid such as water into intestine 133 through an irrigation channel (not shown), and conduit 128 can be used to conduct materials from intestine 133, through distal end 134 of conduit 128, and proximally through conduit 128 and out of the body. Conduit 128 may comprise a material transportation mechanism 137 (not shown in these figures but shown elsewhere herein) for moving such materials through conduit 128 and out of the body.

According to some methods of using cleaner 300, occasionally, (e.g., either periodically and regularly or when flow impediments are detected by a user or by controller 200), closure mechanism 144 is closed, isolating the interior of conduit 128 from intestine 133, and then a pressure differential is created between a medial portion of conduit 128 and a proximal end of conduit 128. This pressure differential, whether of liquid or gas or a mixture of both, purges conduit 128 by pushing its contents toward its proximal end. FIG. 2A shows mechanism 144 open, FIG. 2B shows mechanism 144 closed, and FIG. 2C shows fluid (gas or liquid) optionally being supplied from source 1441 and/or source 1442, and vacuum optionally being applied from source 1443, and creating a pressure differential which causes materials in conduit 128 to flow toward its proximal end and out of the body.

Closure mechanism 144 maybe be closed and opened mechanically (e.g. by a connecting rod, not shown), electromagnetically, or in any other manner. Its closure is optionally commanded by controller 200.

Figure 2D:
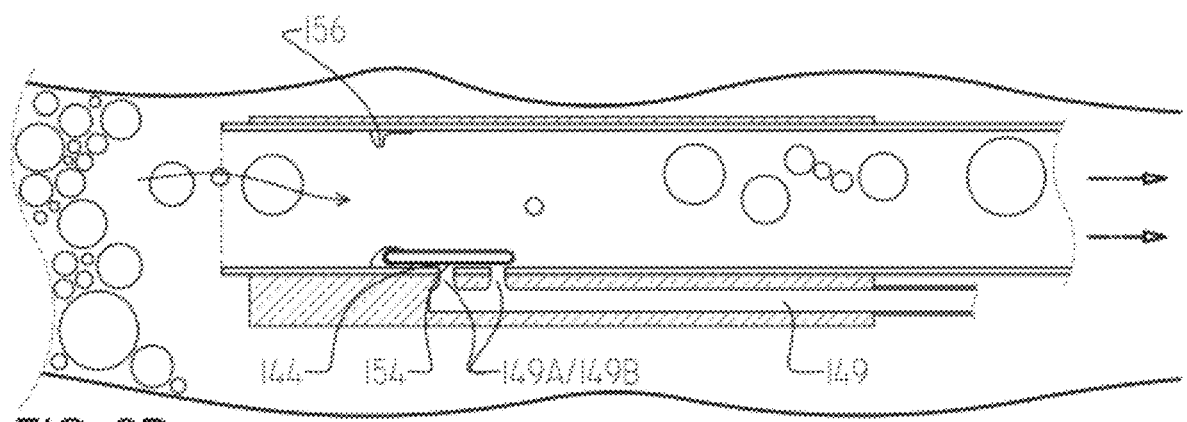
Figure 2E:
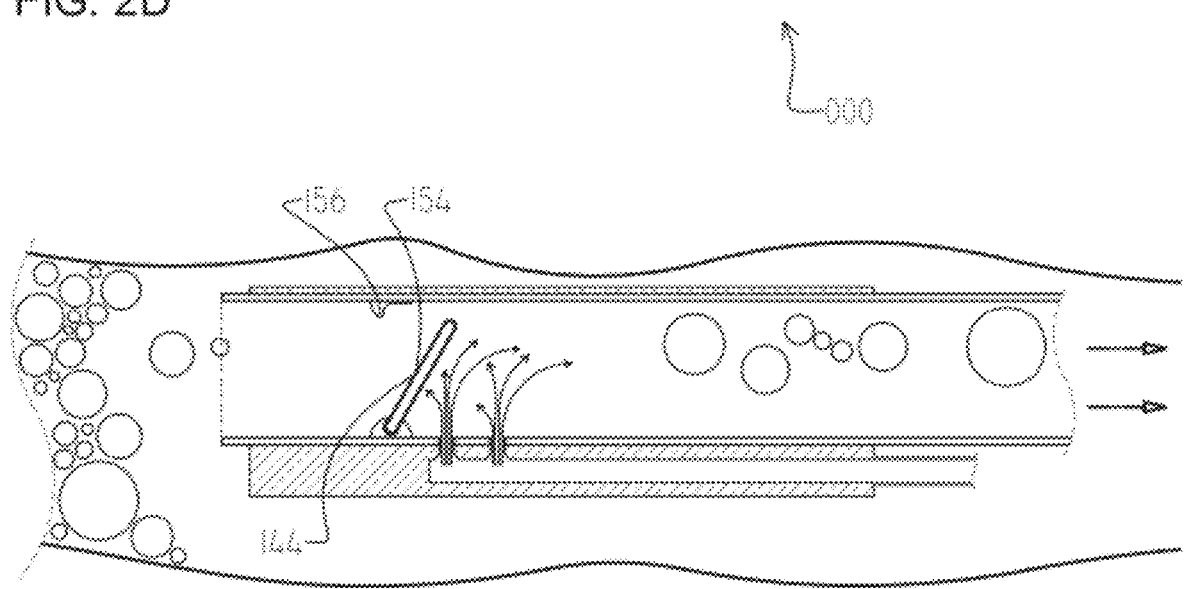
Figure 2F:
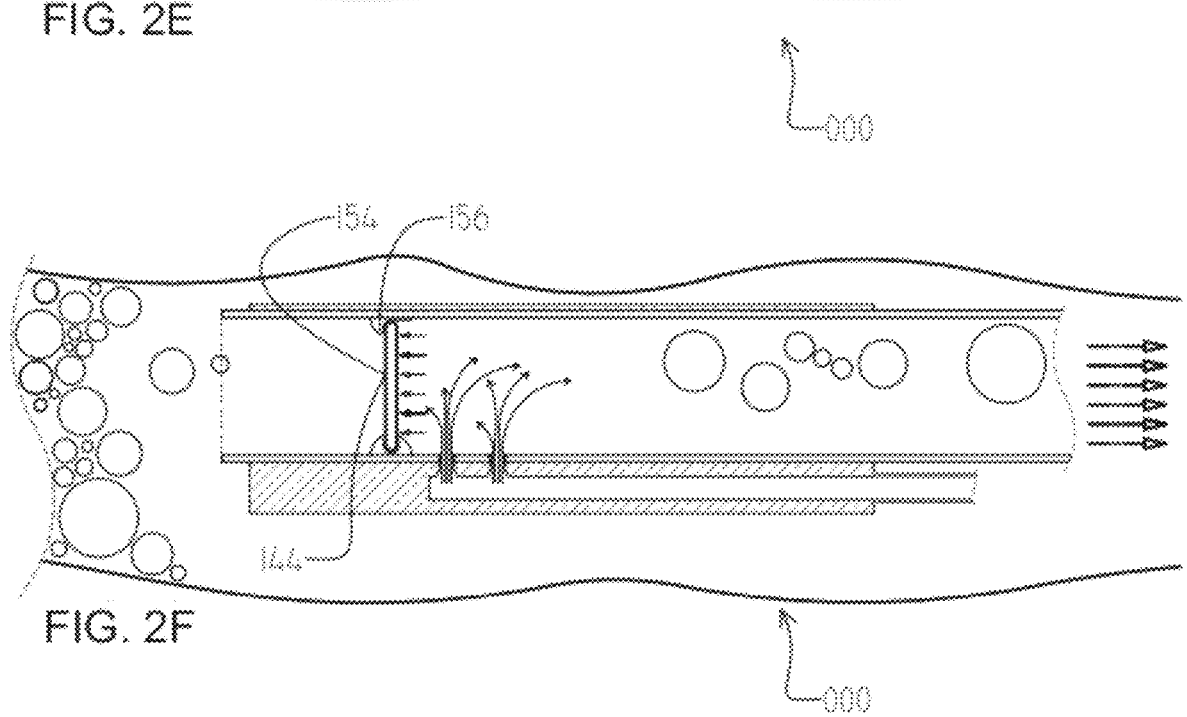

FIGS. 2D, 2E, and 2F show an alternative implementation of closure mechanism 144 which is a one-way valve 154 optionally closed and by hydraulic pressure and optionally opened by hydraulic pressure or by a weak spring (not shown). FIG. 2D shows valve 154 in its open position, where it optionally serves also to close orifices 149. FIG. 2E shows flow of fluid through orifices 249, where hydraulic pressure moves valve 154 toward its closed position. FIG. 2F shows valve 154 in its closed position against a stop 156, where it isolates intestine 133 from influence by fluid flows within medial and proximal portions of conduit 128.

Cleaning Device Using High-pressure Fluid Jets to Shred Matter in an Evacuation Conduit:

Attention is now drawn to FIG. 1, which presents a cleaning device which uses high-pressure water for cutting or otherwise graining fecal materials contained in an evacuation conduit 128, according to some embodiments of the present invention.

Known systems for cleaning a colon use water to irrigate the colon and to wash the colon and/or to dilute or dislodge fecal matter within the colon, and also to wash fecal matter from the colon out of the body through an evacuation lumen.

These devices do not use high pressure fluids to shred nor to move fecal matter. Indeed, water jet power is limited by the FDA, which requires that pressure of water introduced into the colon be sufficiently low to prevent damage to tissues which might be caused by pressure from a water jet. In consequence, feces tends to be liberated from the intestinal walls and from impacted feces portions in chunks which will not easily pass through an evacuation conduit, both because of the size of the chunks and because only low water pressure is provided in the intestine itself.

In an exemplary embodiment of the invention, high pressure jets are used to dismember feces, however, they are contained so they cannot contact and damage tissue. In an exemplary embodiment of the invention, the jets have a velocity of between 0.1 m/s and 10 m/s or more, such as 15 m/s or 20 m/s, or, for example, 1 m/s, 5 m/s, 7 m/s or intervening velocities. Optionally, the velocity and cross-section of the jet is such that the jet would cause damage and/or penetration of GI tissue if impinging on the tissue from a distance of 3 cm or less, optionally even with intervening water. Optionally or alternatively, the pressure used is such that the jet would penetrate and/or damage tissue if the nozzle was in contact with tissue. For example, the pressure may be above 4 bar, above 10 bar, above 20 bar or intermediate pressures. Optionally, the jets include particulate matter, which would damage tissue if hurled at tissue with force, but assist in breaking down feces.

FIG. 1 presents an intestinal cleaning device 130 insertable in an intestine 133 and comprising an evacuation conduit 128. Device 130 uses a high-pressure fluid source 1301 connected to lateral openings 138 into conduit 128 to produce high-speed high-pressure water jets 139 within the protected environment inside conduit 128, to cut or otherwise grain the fecal material contained in conduit 128.

According to some embodiments of the present invention a method for cleaning a colon by drawing fecal matter from a colon in an evacuation conduit method comprises inserting device 130 in a colon, irrigating the colon to liberate fecal material, using suction to draw liberated fecal material into conduit 128, and connecting a source 1301 of high-pressure fluid to lateral opening 138A and 138B to produce a high-velocity fluid jet directed toward the interior of conduit 128, where jets 139 will interact with the liberated fecal matter, reducing in size pieces of the liberated fecal matter and thereby facilitating drawing said fecal matter from said colon through said conduit.

Device 130 comprises a fluid input conduit 136 proximally connected to a fluid source, optionally high-pressure 1301 and distally connected to lateral openings 138 in a wall 131 of exhaust conduit 128 of device 130. When high pressure fluid (e.g. water) is allowed by a valve 1302 (optionally remotely controlled by a controller 1303) to pass into fluid input conduit 136, passage of the high-pressure fluid through opening 138A and optional additional openings 138B creates high-speed high-pressure fluid 'jets' 139 aimed at contents of exhaust conduit 128. In some embodiments jets 139 are aimed away from all distal openings 132 of exhaust conduit 128, thereby protecting body tissues outside openings 132 from exposure to direct contact with jets 139.

Exhaust conduit 128 may optionally comprise a matter transportation mechanism 137 for transporting matter out of the body through conduit 128. In an exemplary embodiment shown in FIG. 1, mechanism 137 is embodied as a helical spring 1371.

Device 130 also has an optional second fluid input pipe 135 for introducing a fluid 1351 (typically water) into intestine 133 at a pressure low enough to avoid damage to the GI wall.

Openings 138 are so positioned and so constructed that jets 139 are so directed that should lumen 128 be free of intervening material objects such as feces, jets 139 are directed towards walls 131 or towards internal components of device 130 (such as transporting mechanism 137) within lumen 128, and are not directed towards distal opening 132.

In an exemplary embodiment of the invention, a method using device 130 comprises directing high pressure jets of water or other fluid toward fecal matter or other objects within lumen 128. Low-volume high-pressure fluid flows are used, as these have an effective cutting or shredding effect on such materials. Body tissues outside device 130 are not subject to high pressures because jets 139 are directed towards internal parts of device 130 and not towards distal opening 132, and those body tissues are not subject to massive and/or penetrating fluid flow as a result of this process because high-pressure low-volume flows are used.

High velocity jets 139 produced in device 130 can act as cutters and shredders, and can have the effect of breaking large chunks of feces into smaller chunks more easily transported and less likely to clog exhaust lumen 128. Intestinal tissues are protected from the force of the fluid jet because the process takes place within the device 130 and not in the open GI lumen, and if no feces are present to take the brunt of the high-pressure fluid flow, the jets 139 will hit the hard wall 131 of lumen 128 and bounce back or be otherwise diffused, and consequently will not damage intestinal tissue.

In an exemplary embodiment of the invention, a shredding section of the device is between 2 and 20 cm long, for example, between 3 and 7 cm long. Optionally, over such a section, if, for example, an axial rotating shredding coil (e.g., FIGS. 5A-5C) is used for shredding, the spacing between coils goes down by between 20% and 90%, for example, 50%, or more. Optionally or alternatively, over such a section the diameter of the coils can increase by a factor of, for example, between 2 and 6. In an exemplary embodiment of the invention, the initial diameter and spacing between coils is 3 mm and 10 mm respectively. In some embodiments, the initial spacing between coils is small and then grows and then optionally decreases. In an exemplary embodiment of the invention, the speed of rotation of the coil is between 1 and 7000 rotations per minute, for example, between 3000 and 5000, or more, optionally controllable by an external circuit and user input and/or be set by a manual rotation speed.

In an exemplary embodiment of the invention, between 2 and 10 jets are provided, optionally with spacing of between 2 mm and 30 mm between adjacent jets. Optionally, the jets are at different axial positions along the lumen. Optionally or alternatively, the jets are at different circumferential positions.

Conveying and/or Shredding Matter within an Exhaust Conduit

Figure 5A:
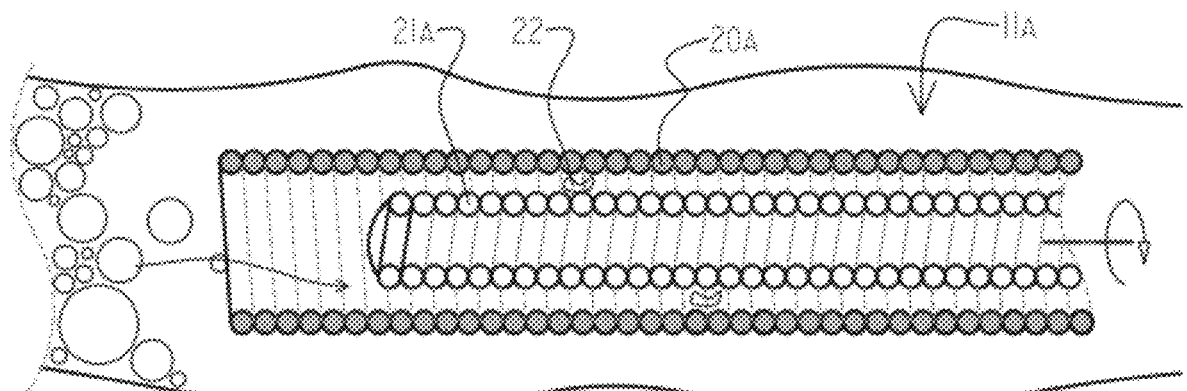
FIGS. 5A-5F show processes for conveying matter out of an exhaust conduit of a cleaning device, and for breaking conveyed matter into small pieces for easier transport, according to some embodiments of the present invention.
Figure 5B:
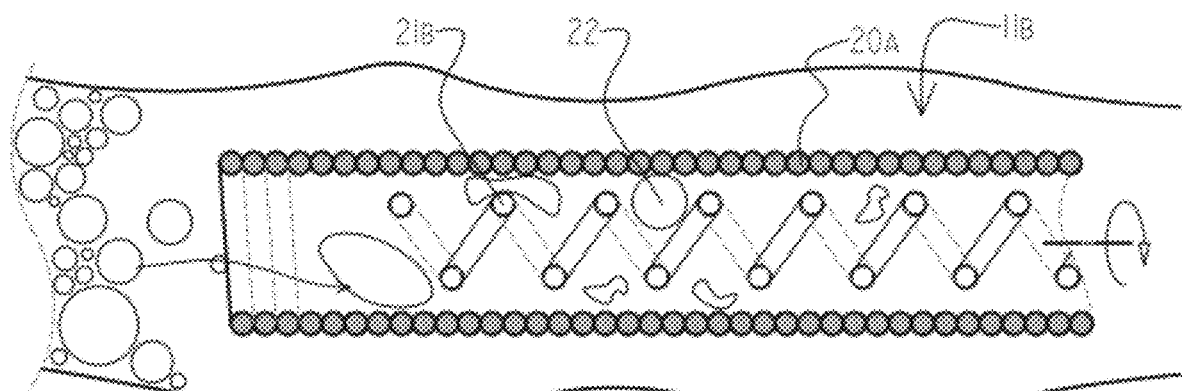
Figure 5C:
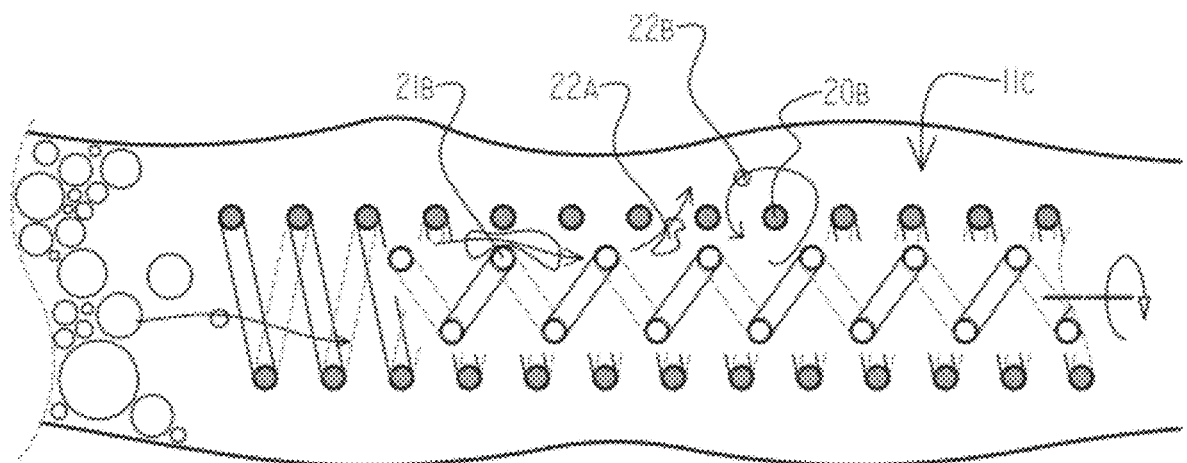

Attention is now drawn to FIGS. 5A-5C, which show processes for conveying matter out of an exhaust conduit of a cleaning device, and for "graining" that matter (i.e. breaking conveyed matter into small pieces for easier transport).

FIG. 5A presents a cleaning device 11A in which an inner spring 21A whose windings are wound tightly one against another is positioned within an outer spring 20A whose windings are also positioned tightly on against another, as shown in the figure. Both inner spring 21A and outer spring 20A have what is sometimes called a "zero" gap or step between spring helix windings, meaning that no space is left between successive windings, as shown. In use, inner spring 21A is rotated, producing the effect of moving pieces of fecal matter 22 proximally and eventually causing them to exit the body. Rotation of inner spring 21*a* grains and moves fecal parts 22 from the body's cavity and outside it. As shown in the figure, inner spring 21A and outer spring 20A are typically fabricated to be wound in opposite directions, one clockwise and the other counter clockwise. Physical interactions of matter pieces 22 with moving inner spring 21A and static outer spring 20A both transport material pieces 22 proximally but also tend to break pieces 22 into smaller pieces through frictional interactions between pieces 22 and the inner and outer springs. However, the system of FIG. 5A produces only a low speed in transporting matter proximally out of device 11A, and room is available to handle only small pieces of fecal matter 22 because only small pieces will fit between the inner and outer springs.

Using outer spring 20A with a "zero gap" is safe so long as device 11A is positioned in a straight line, but may become unsafe if device 11A is forced into a curved path, as is typically the case in processes of cleaning an intestine. One danger is that portions of intestinal wall can become injured when curving of outer spring 20A creates a gap between spring windings, into which space a portion of intestinal wall can become caught and be injured. This problem is discussed in detail in U.S. Pat. No. 4,923,460.

FIG. 5B illustrates a cleaning device 11B with an inner spring (21B) with "wide" gaps or steps between each winding of the spring helix. In this embodiment outer spring 20A has a zero-gap winding as shown in FIG. 5A. Rotating wide-gap inner spring 21A can be effective in transporting material in a proximal direction because the wide 'steps' of inner spring 21A advance material rapidly when spring 21A is rotated, and device 11B can handle large fecal pieces 22 since wide-spaced inner spring 21A allows room for them, but there is little "graining effect" (breaking large fecal pieces into small pieces) because the wide gaps of the inner spring don't tend to force fecal pieces 22 against outer spring 20A.

FIG. 5C presents a cleaning device 11C wherein an inner spring 21B with "wide" gaps or steps between spring helix windings interacts with an outer spring 20B also having a "wide" gap. This design has the disadvantage that it conveys matter poorly because of the gap between the outer spring helix windings: if fluid or small fecal parts are moved proximally by inner spring 21B and encounter resistance due to colon geometry or other factors, then fecal parts and fluids will tend to escape from between windings of outer spring 20B as shown at label 22A of FIG. 5C, and may even move backwards and reenter outer spring 20B at a more distal position, as shown at label 22B. In other words, device 11C may not function efficiently as a machine for graining and conveying fecal matter. Moreover, an outer spring 20B with "wide gaps" between windings may be unsafe since the colon wall could easily catch inside such windings and be damaged and even perforated.

Figure 5D:
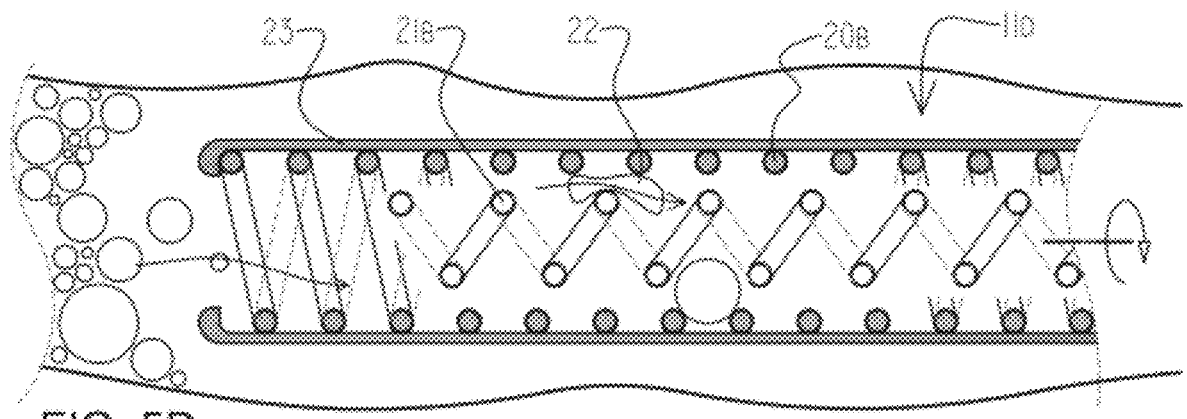
Figure 5E:
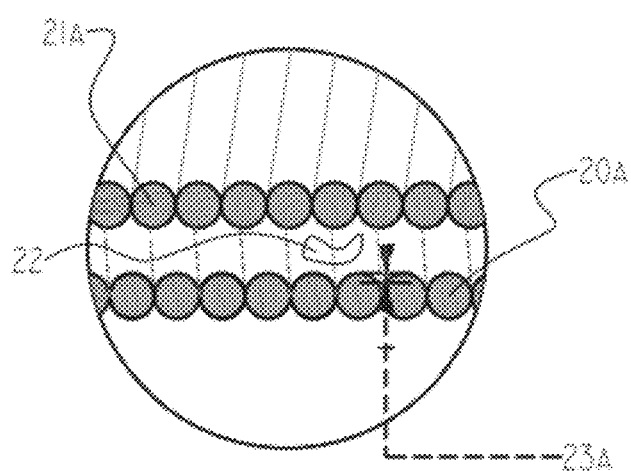
Figure 5F:
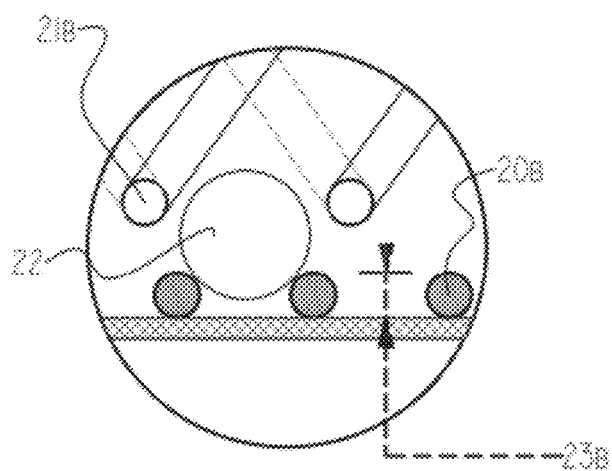

FIGS. 5D-5F present devices for transporting and graining fecal matter according to embodiments of the present invention. FIG. 5D presents a device 11D which is similar to device 11C shown in FIG. 5C, but differs therefrom in that the described apparatus is contained within a flexible outer pipe or tube 23, which is absent in FIGS. 5A-5C. Tube 23 prevents the unwanted effects described above with reference to FIGS. 5A-5C. Fecal matter and fluids move proximally in a highly efficient manner, the hazard of a colon wall touching or being caught in the inner or outer springs is eliminated, and the system can provide both high graining power and fast conveying speed.

In some embodiments tube 23 has a smooth exterior surface and a non-smooth or abrasive interior surface which defines an exhaust lumen. The non-smooth interior of wall 23 can be formed as a helical form glued or welded an inner side of wall 23, the helical form being wound either in the same direction as a helical inner spring 21B, or in an opposite direction. In some embodiments these windings are at least 0.5 mm apart. An inner spring 21B of this embodiment can be formed as described above for devices 11B and 11C. In some embodiments windings of inner spring 21B are also at least 0.5 mm apart.

Alternatively, inner spring 21B may be embodied as any other form of object positionable within pipe 23 and operable to rotate and to advance and retract freely within pipe 23, such as a helical brush or other form of brush, a paddle, a propeller, or any other rotatable object.

FIG. 5E shows a graining effect as that might be created by device 11A of FIG. 5A. A small fecal part 22 between the outer spring 20A and inner spring 21A encounters only a minor graining effect because the 'ridges' encountered by part 22 are small. In contrast, FIG. 5F shows large ridges presented by windings of spring 21B, which large ridges produce a strong graining effect, while spaced-apart windings of spring 21B in this embodiment enable large feces pieces 22 to be handled.

Figure 6A:
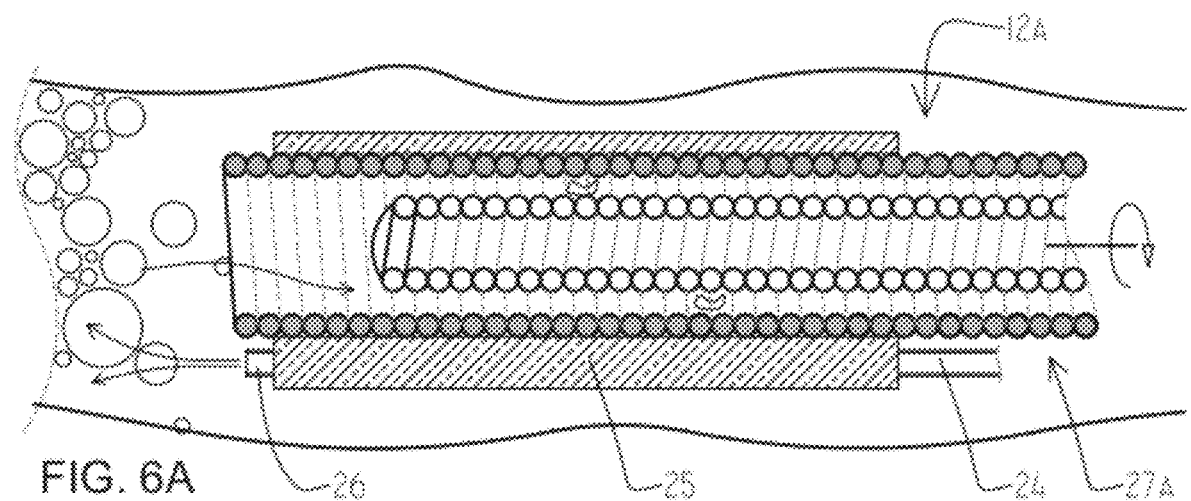
FIGS. 6A and 6B present a cleaning device which provide water jets for irrigating an intestine, according to some embodiments of the present invention.
Figure 6B:
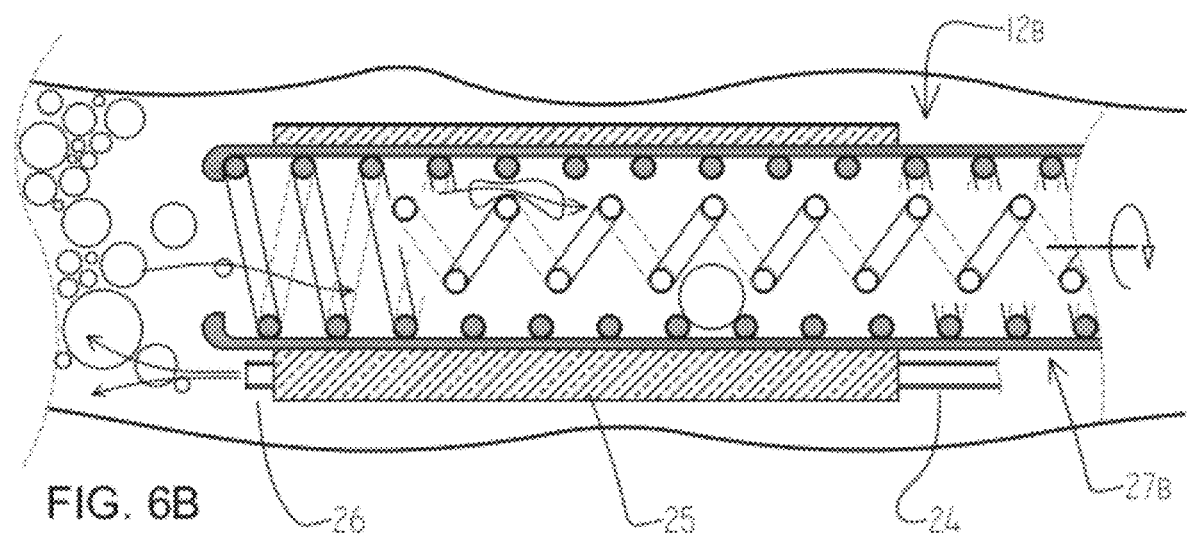

FIGS. 6A and 6B present a cleaning device 12A which comprise water jet production units in which fluid inserted via a pipe 24 from a water source passes through lumens of a housing 25 and emerge from a nozzle 26 into an intestine. Water jets emerging from nozzles 26 can be used to break down fecal matter into small parts which can then be transported distally out of the body. Water jet production units may be comprised in any of the embodiments presented herein.

Exemplary Embodiments for Graining and/or Exhausting Fecal Matter:

Attention is now drawn to FIGS. 4A-4F, which present embodiments which include features that facilitate 'graining' of fecal matter within an evacuation conduit of a cleaning device by creating turbulence within the conduit and by grinding and cutting the pieces and by pulling them apart by subjecting them to contradictory pulling forces.

FIGS. 4A-4F present cleaning devices each having a multi-lobe exhaust lumen which comprises a plurality of co-aligned lobes running side by side along at least a portion of the length of the lumen, according to embodiments of the present invention.

Figure 4A:
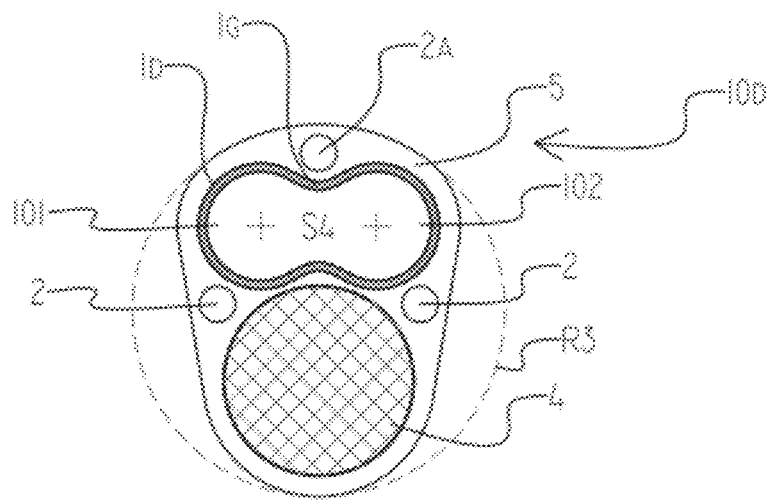
FIGS. 4A-4F present cleaning devices each having a multi-lobe exhaust lumen which comprises a plurality of co-aligned (substantially parallel) lobes running the length of the lumen, according to some embodiments of the present invention.

FIG. 4A shows a device 10D comprising within a housing 5 an (optional) endoscope optic 4, one or more fluid input conduits 2, and a matter exhaust lumen 1D shaped within housing 5 and which comprises a first lobe 101 and a second lobe 102. Lobes 101 and 102 are in fluid communication along at least a part of their length, which is to say that fluid and other matter can flow between them. Each lobe has a central axis (shown as a "+" in the figure) and optionally has a cross-section at least part of which has a circular border, as shown in FIG. 4A. Lumen 1D as a whole has a roughly "figure 8" shape, optionally providing room for a fluid input lumen 2A as shown in FIG. 4A.

Figure 4B:
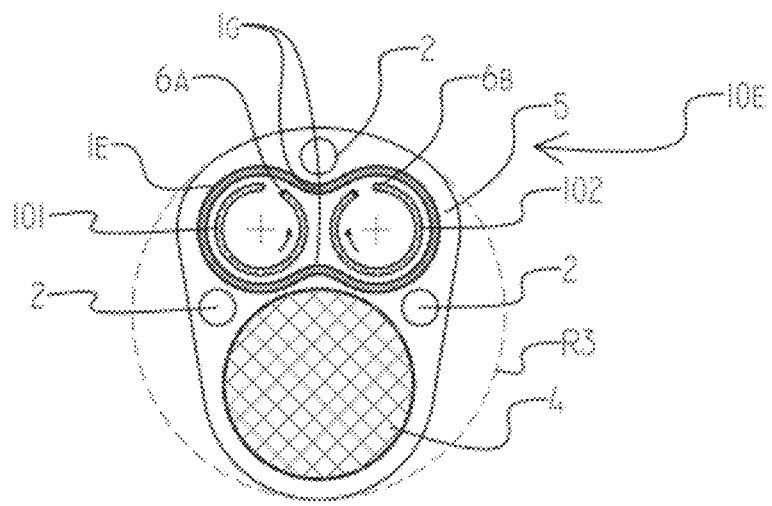

FIG. 4B shows a cleaning device 10E wherein a two-lobed exhaust lumen 1E contains a rotatable device in one or in both lobes. FIG. 4B shows a rotatable device 6A in lobe 101 and a rotatable device 6B in lobe 102. It is to be understood however that device 10E may comprise one rotatable device or two.

Lobes 101 and 102 are open to each other, in the sense that fluid communication between them is possible along at least a portion of their length.

Lobes 101 and 102 are sized and shaped with respect to helical devices 6A and 6B in such a way that devices 6A and 6B are independently rotatable each within its lobe, and are also optionally able to independently advance and retract each within its lobe. However, a 'shoulder' 1G, or other similar formation, prevents devices 6A and 6B from moving from moving 'sideways' from one lobe into another.

In some embodiments devices 6A and 6B can be rotated in the directions shown by the small arrows in FIG. 4B: clockwise in lobe 101 and counterclockwise in lobe 102. In some embodiments both can be rotated in directions opposite to those shown in the figure, i.e. counterclockwise in lobe 101 and clockwise in lobe 102. These directions cause portions of devices 6A and 6B which approach each other within their common lumen 1E to approach a parallel movement where they are closest together, and then to pull apart.

Alternatively, in some embodiments devices 6A and 6B can be rotated in opposing directions (i.e. clockwise in both lobes or counterclockwise in both lobes), which causes the two devices 6A and 6B to be moving in opposing directions where they are at their closest approach. Additionally, in some embodiments one or both rotatable devices can be caused to alternate rotational direction.

In some embodiments, devices 6A and 6B are helical devices (also designated 6A and 6B. If device 1E is inserted in an intestine, rotation of a helical device in one direction serves to pull matter towards the intestine, while rotation in the opposite direction serves to pull matter away from the intestine. Rotating one helical device in a direction which pulls matter towards the intestine and rotating the other in a direction which pulls matter away from the intestine will create shearing forces which will contribute to graining of matter caught between the helices.

In general, that diversity of movements described above (pulling towards intestine or away, rotating the create parallel movement or opposite movement, and independently moving helices or other rotating devices forward and backward in their lumen) create pulling, pushing and cutting forces which can serve to cut, grind, and otherwise grain material within lumen 1E.

Figure 4C:
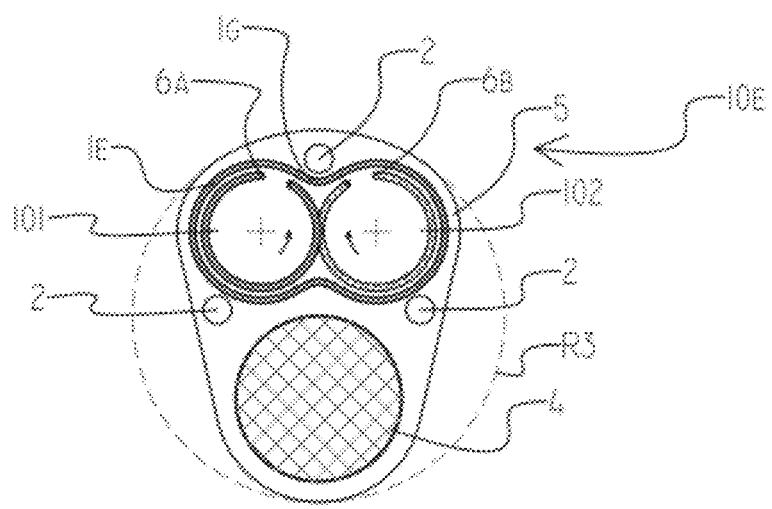

In some embodiments, additional graining effects can be produced when helical devices 6A and 6B are caused to overlap, as is shown in FIG. 4C. Overlapping helical devices can provide efficient pumping action and can also contribute to shredding the content of lumen 1E.

Helical devices 6A and 6B can be helical springs, can be rods or pipes surrounded by a helical thread can be formed as a helical brush similar to those used to clean colonoscope working channels, or can be a wire or a rope wire made from stainless steel or another material.

Components having forms other than helical can also be used in one or both of lobes 101 and 102. An example is given in FIG. 4D, where two paddle-shaped forms 106A and 106B are provided in place of helical devices 6A and 6B. (Rotating paddles create turbulence which generates shearing and tearing forces. shape may also be used, and labels 106A and 106B should be understood to refer to these shapes also. In general any shape may be used which provides turbulence within lumen 1E and/or which tends to propel materials proximally within lumen 1E.

Figure 4D:
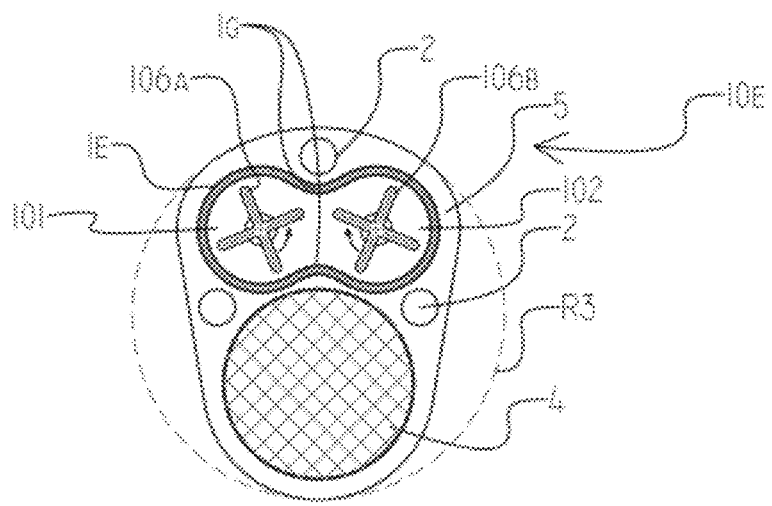

It is noted also that the shapes used in lumen 1E can vary along the length of the lumen. For example, a paddle shape as shown in FIG. 4D could be provided at a distal end of lumen 1E, a propeller shape could be provided distal to the paddle shape along the same axes of lobes 101 and 102, and a helical devices could be provided at more proximal portions of those lobes. If we refer to all these shapes extending the length of lobes 101 and 102 as "driving devices", then in some embodiments device 10E may be provided with a variety of driving devices from among which a user may select the combination he wishes to used depending on characteristics of the patient or any particular desired effect or desired optimization of the cleaning process. In general, in some embodiments each driving device is free to rotate within its lobe and/or may be free to independently advance and retract within its lobe, yet each driving device is constrained so that a longitudinal axis of each driving device is retained (by the shape of lumen 1E) within one of the lobes.

Figure 4E:
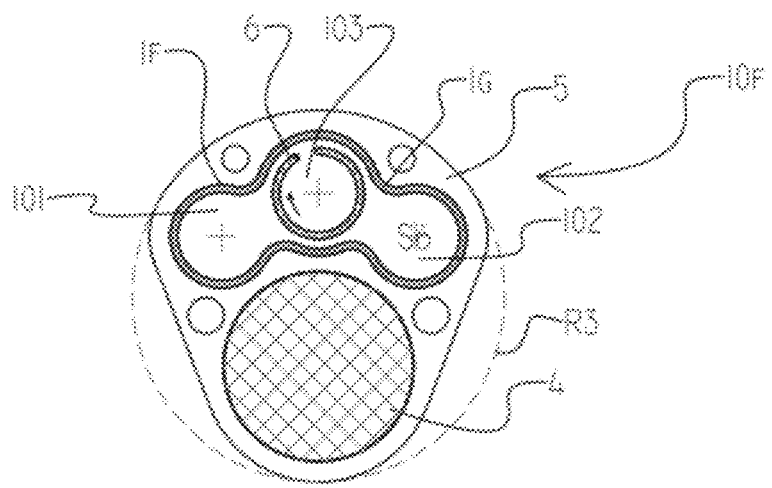

FIG. 4E provides an additional alternative embodiment, wherein more than two lobes are used in an exhaust conduit 1F. Note that in these embodiments as well as in the other embodiments shown in FIGS. 4A-4F, each lobe may contain a driving device, or alternatively only some lobes may comprise a driving device and others may be empty of devices and available for the moving exhaust matter itself. FIG. 4E shows a central lobe 103 which comprises a driving device (shown as a helical device 6), while side lobes 101 and 102 are empty.

Figure 4F:
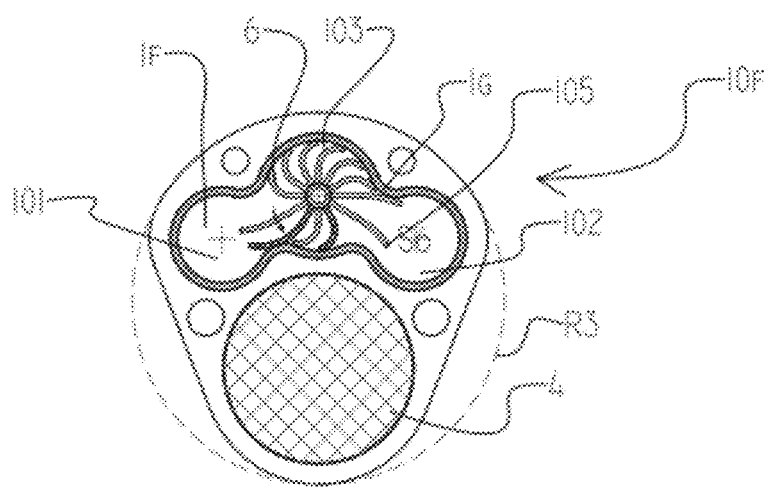

FIG. 4F shows an embodiment similar to that of FIG. 4E, but wherein a driving device is embodied as a rotatable brush 105 within lobe 103 but whose flexible bristles are long enough to penetrate into side lobes 101 and 102, thus providing empty space in lobes 101 and 102 to facilitate transportation of objects out of the body, while also providing a source for driving power and a source of turbulence and possibly shredding and cutting activities accomplished by bristles from brush 105.

Figure 6C:
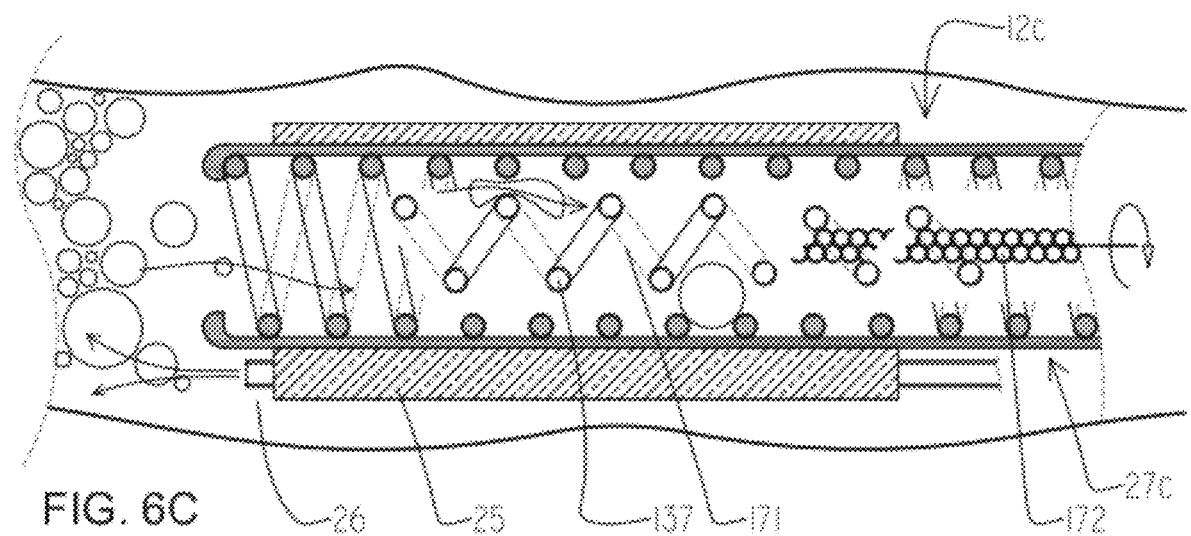
FIG. 6C presents a cleaning device with a material transportation mechanism which comprises an active distal head and a medial power train, according to some embodiments of the present invention.

Rotational Tool within an Evacuation Conduit having a Distal Operating Portion and a Proximal Power Transfer Portion Various figures of the instant application present helical tools and other rotational tools positioned within an evacuation conduit useable to grain fecal matter and/or to propel it out of the body. In some embodiments such rotational tools extend the length of the evacuation conduit. In some embodiments it has been found efficient to use a tool with a distal operational portion and a proximal power transfer portion whose primary function is to transfer rotational power or other power to the distal portion. FIG. 6C presents such a tool according to some embodiments of the present invention.

FIG. 6C presents a cleaning device 12C which has an exhaust lumen 128 which contains a tool 137 having a distal operational portion 171 designed to grain material and/or to propel said material in a proximal direction within lumen 128. Mechanism 137 also comprises a medial portion 172 which comprises a rope or rod or other flexible connector designed to transfer rotational power from a proximal motor or other energy source (not shown) to distal portion 171.

Using Multiple Conduits and Shaped Conduits to Reduce Overall Cross Section of a Cleaning Device:

A device used to clean a colon must pass the anal spincter and/or a speculum to enter the colon. Once in the colon, the device must be maneuverable within the colon, which includes several sharp curves. A device with reduced cross-section is desirable.

Figure 3A:
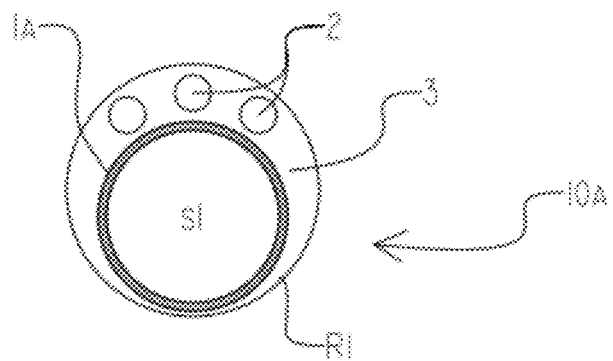
FIGS. 3A-3C present cleaning devices using multiple fluid input pipes and/or flattened exhaust lumens to reduce device cross-sectional area of the devices, according to some embodiments of the present invention.
Figure 3B:
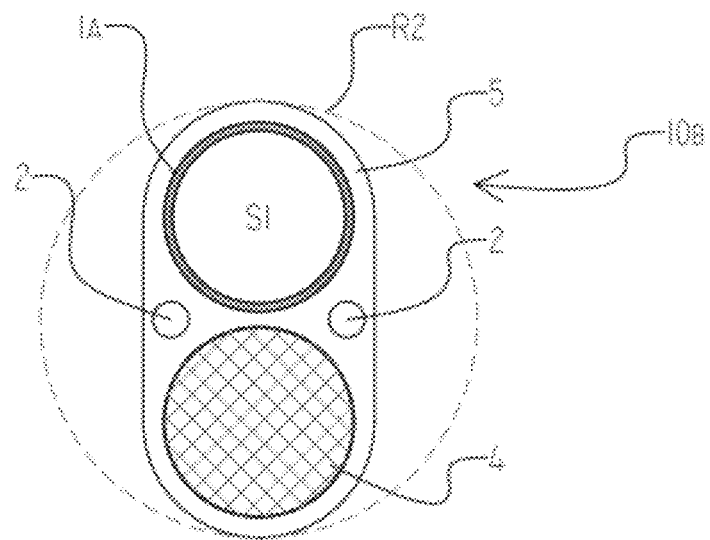
Figure 3C:
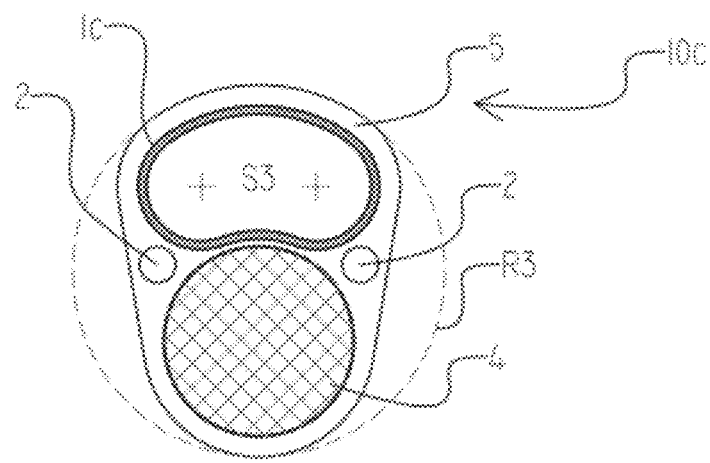

Attention is now drawn to FIGS. 3A-3C, which present cleaning device configurations in which multiple input conduits are used to reduce the device cross-section, according to some embodiments of the present invention.

A cleaning device 10A presented in FIG. 3A comprises an evacuation lumen 1A having a cross-section diameter S1. A housing 3 (for example an extrusion housing) comprises a plurality of fluid input conduits 2 usable to introduce water into a colon. The overall diameter of device 10A is R1. Evacuation lumen 1A may comprise a matter transportation mechanism such as mechanism 137 discussed with reference to FIG. 1.

FIG. 3B presents a cleaning device 10B which comprises an endoscope or a colonoscope 4. Endoscope 4 is constructed together with, or attachable to, an evacuation lumen 1A having a cross-sectional diameter S1. A housing 5, optionally an extrusion housing, comprises a plurality of fluid input conduits 2 usable to insert water into a colon. The maximum diameter of device 10B is the diameter of circle R2 seen in FIG. 3B. Evacuation lumen 1A of FIG. 3B is shown as identical in diameter to evacuation lumen 1A shown in FIG. 3A, yet overall device diameter (the diameter of circle R2 of FIG. 3B) is greater than overall device diameter (the diameter of circle R1) of FIG. 3A. The diameter of a colon is limited, and a large-bore device like that shown in FIG. 3B could be problematic in several respects: it would tend to be stiff, difficult to steer, and could cause pain and retard recovery by damaging the intestinal wall of a patient.

FIG. 3C provides a device 10C which comprises an endoscope 4 and an evacuation lumen 1C shaped as a flattened and slightly curved ellipse whose cross-section S3 is shown in the figure. Flattened lumen 1C is advantageous over cylindrical lumen 1A of FIG. 3B because an overall diameter of device 10C (diameter of circle R3 of FIG. 3C) is smaller than the overall diameter (diameter of circle R2) of device 10B, for an identical evacuation lumen cross-sectional area.

Preventing Exposure of Tissue to Excessive Pressure due to over-inflation of an Intestine:

Inserting fluid into a colon (e.g. by use of the devices of FIGS. 6A and 6B) can result in dangerously high fluid pressures within the intestine, possible leading to ruptures or other tissue damage.

Figure 7A:
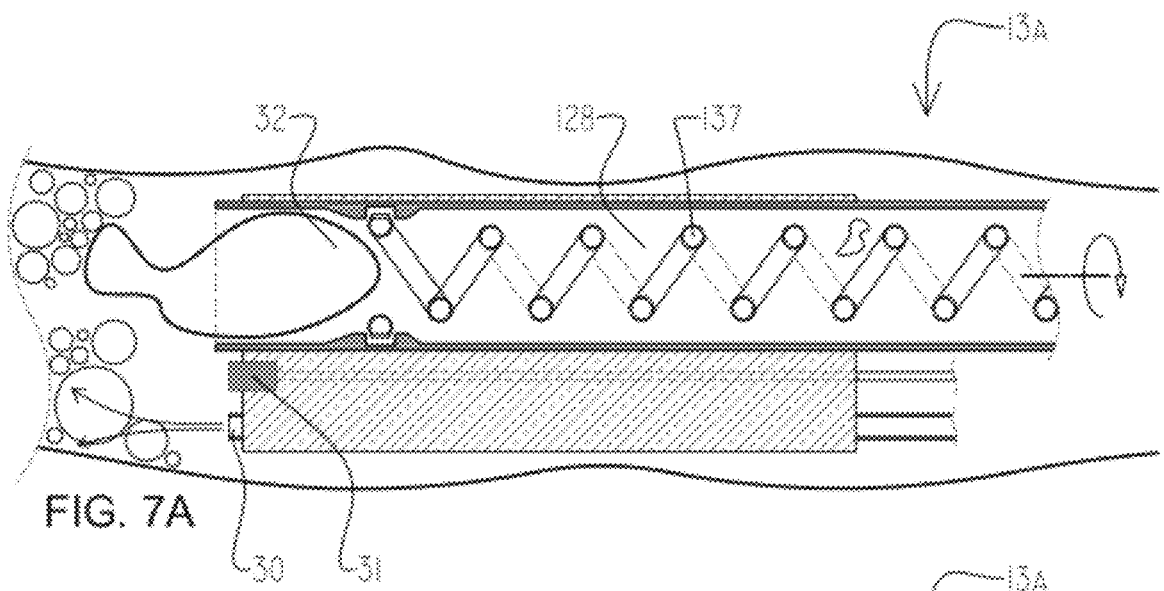
FIGS. 7A-7D present cleaning devices using pressure sensors to provide safety features, according to some embodiments of the present invention.

Attention is now drawn to FIG. 7A which presents a cleaning device 13A which protects against inducing excessive pressure in an intestine, according to some embodiments of the present invention.

Device 13A is a cleaning device for cleaning an intestine which comprises a conduit for delivering a fluid to said intestine, a pressure sensor 31 operable to measure ambient pressure in said intestine, and a controller 200 configured to control delivery of fluid through said fluid delivery conduit as a function measured intra-intestinal pressure measured by sensor 31.

Device 13A comprises an evacuation conduit 128 which comprises a matter transportation mechanism 137 and a fluid input nozzle 30. FIG. 7A shows a situation in which nozzle 30 is supplying water into an intestine but a large block of feces 32 is preventing conduit 128 from emptying that water from the intestine. A serious rise in pressure in the intestine could result, causing damage and even possible rupture of the intestine.

To prevent excessive pressure in the intestine, 13A comprises a pressure sensor 31 operable to measure ambient pressure in the intestine. Sensor 31 reports to a controller 200 (shown in FIG. 7D). Controller 200 is configured to cease delivery of water through nozzle 30 if pressure measured at sensor 31 becomes dangerously high, or if the measured pressure exceeds some predetermined amount. Alternatively, controller 200 may attempt to solve the problem by applying suction to nozzle 30 to remove water from the intestine, or by purging lumen 128 using methods discussed elsewhere in this disclosure.

Preventing Exposure of Tissue to Dangerously Low Pressure When Suction is Created in an Evacuation Conduit:

If a cleaning device which comprises a matter transportation mechanism 137 within a rapidly transports a large piece of feces away from a distal end of the cleaning device at a time when that distal end is blocked or partially blocked by fecal debris, a vacuum may be produced in the exhaust lumen of the device. Other processes connected with cleaning may also create a strong vacuum within the evacuation conduit.

Such a vacuum can expose intestinal tissues to forces strong enough to draw the tissues into the cleaning device and/or damage those tissues as a result of that strong suction.

FIGS. 7B-11 present embodiments having features which relate to this problem, according to some embodiments of the present invention.

Figure 7B:
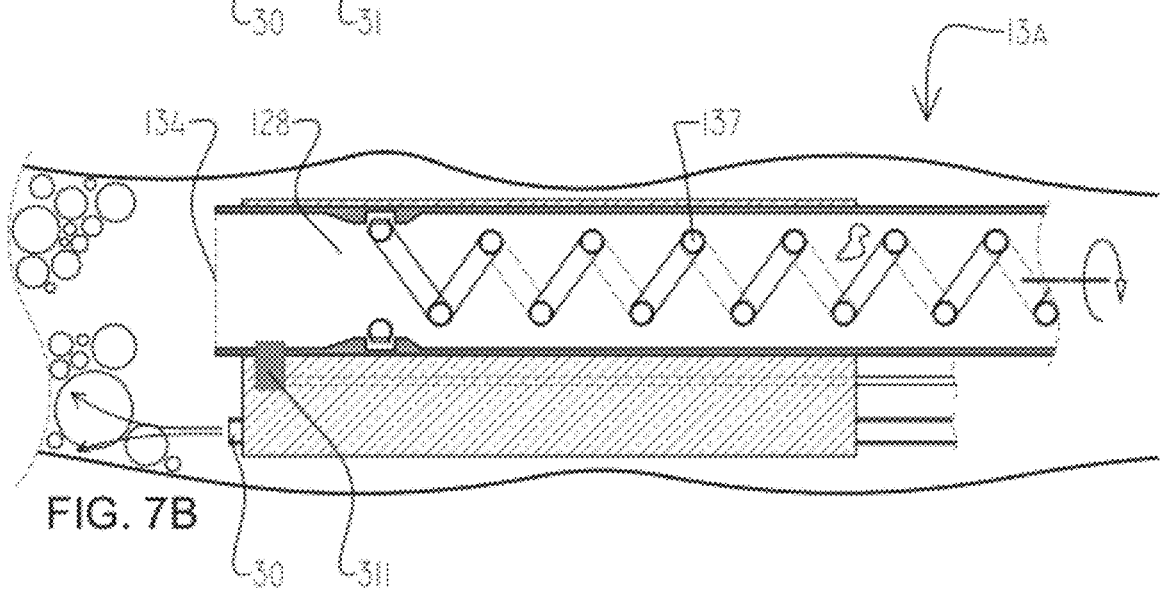
Figure 7C:
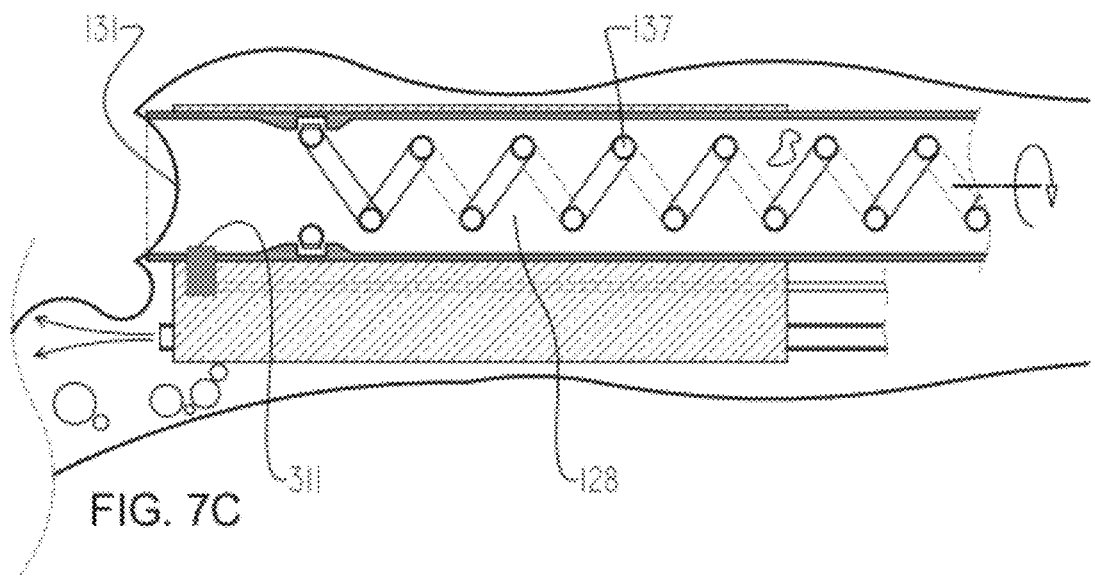

FIG. 7B presents a cleaning device in which a pressure sensor 311 is positioned within lumen 128, optionally near its distal end. Sensor 311 can be used to detect dangerously low pressure in lumen 128. If, for example, a distal opening of lumen 128 were to come to press up against an intestinal wall 131 as shown in FIG. 7C, preventing fluid from within the intestine from flowing into lumen 128, continued operation of transport mechanism 137 could cause low pressure within lumen 128, particularly if a large piece of fecal matter were rapidly transported along the length of lumen 128 by mechanism 137. To deal with this situation sensor 311 is provided to report to a controller 200 (shown in FIG. 7D) that dangerous low pressure exists in lumen 128. Controller 200 can then be configured to cease operation of mechanism 137 under these circumstances, command purging of the evacuation conduit, or to take any other corrective action available to it.

Figure 7D:
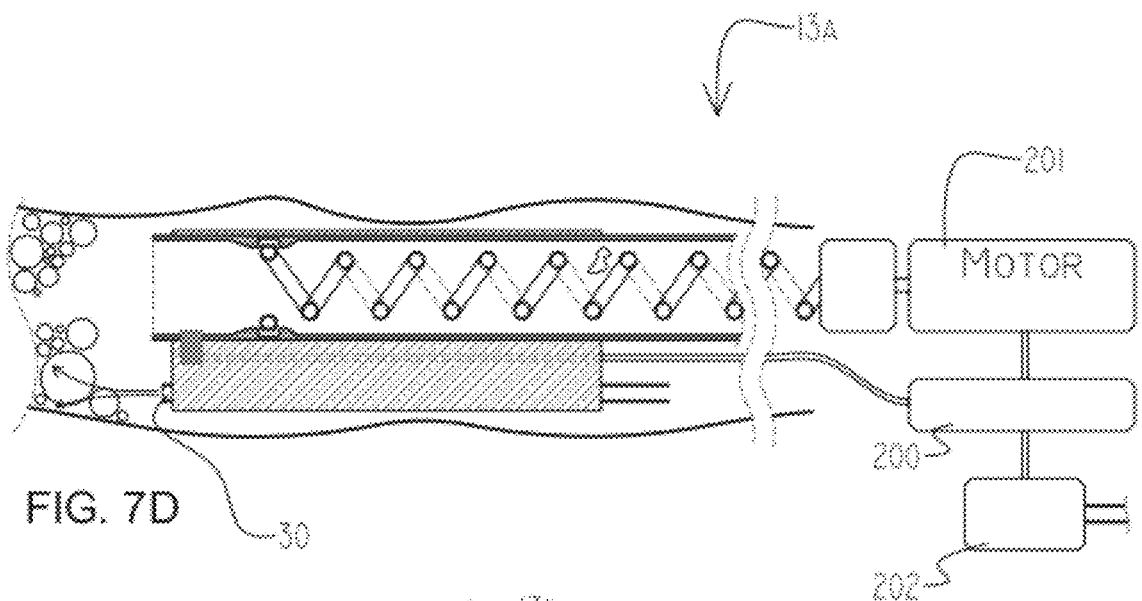

FIG. 7D shows controller 200 connected and configured so as to be able to control water input to nozzle 30 by means of a valve 202 on the water input supply conduit, and/or to be able to control action of transport mechanism 137, and in particular to cause mechanism 137 to cease operation or to reverse direction if pressure sensor 311 detects a pressure which falls below a predetermined value, indicating a dangerous drop in pressure within lumen 128.

Figure 8A:
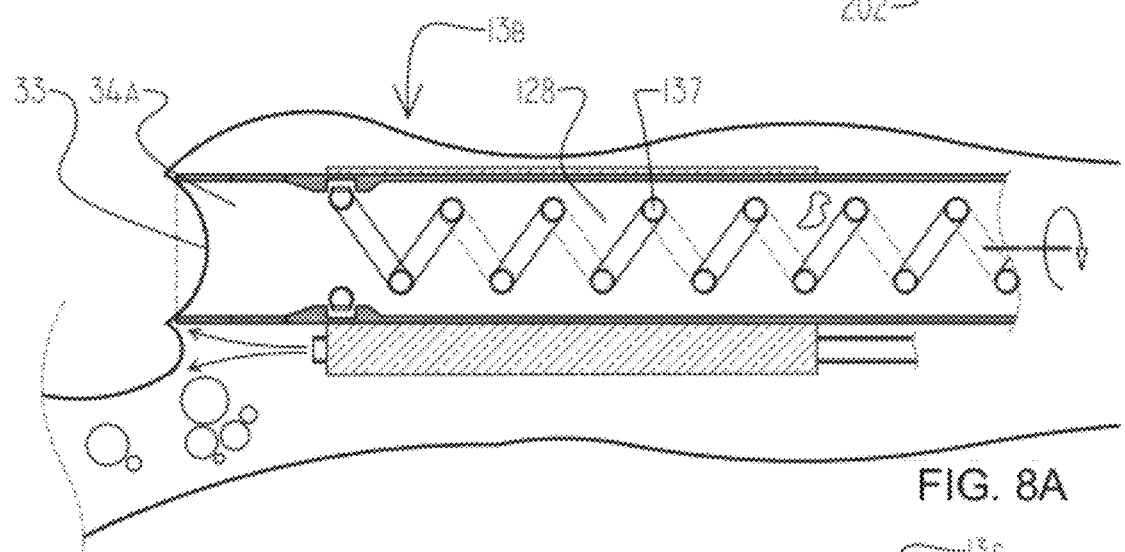
FIGS. 8A and 8B illustrate use of a fluid bypass to prevent dangerous pressure vacuum in an exhaust lumen of a cleaning device, according to some embodiments of the present invention.
Figure 8B:
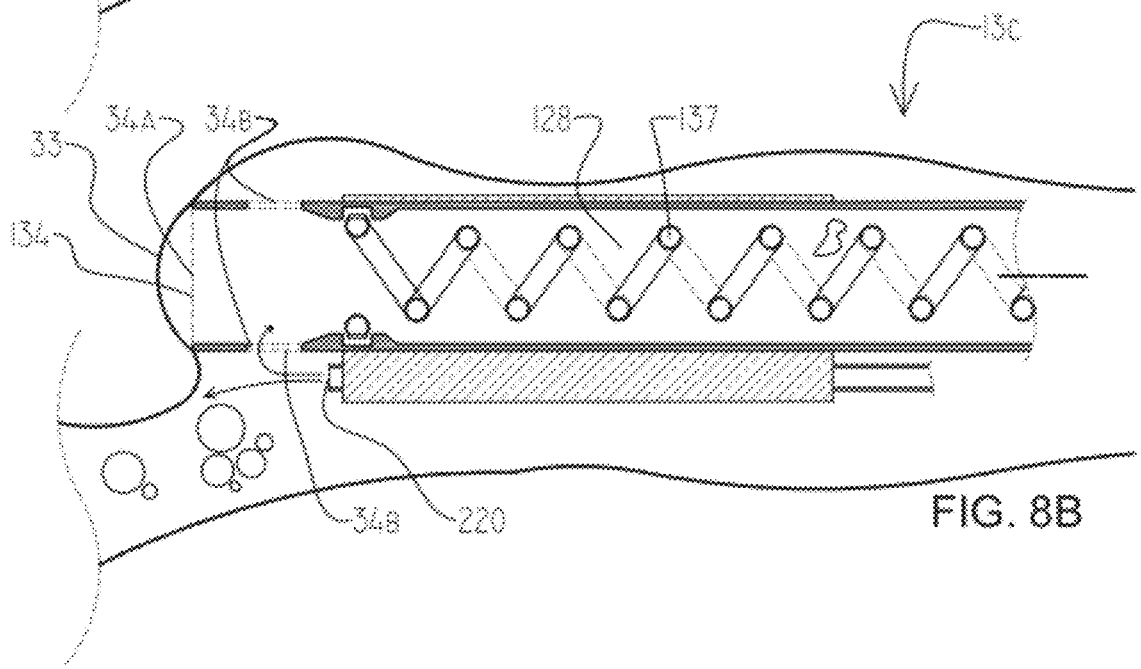

FIGS. 8A and 8B illustrate an alternative method and device for preventing tissue damage caused by a vacuum inadvertently generated in an exhaust lumen 128. FIG. 8A reproduces the dangerous situation discussed in reference to FIG. 7C, where action of a matter transport mechanism 137 within a lumen 128 creates a vacuum and the intestinal wall is drawn towards and into a distal end of lumen 128 and is in danger of being damaged by the suction therein. FIG. 8A shows a construction where no fluid bypass is present. This may be contrasted to FIG. 8B which presents a configuration according to an embodiment of the present invention, wherein additional and optionally lateral openings 34B to lumen 128 are provided, providing passage into lumen 128 from other portions of the intestine, raising pressure therein. Optionally but preferably, at least one opening 34B is positioned near a water source 220. In case of blockage of distal end 134 of lumen 128 (e.g. by suction drawing an intestinal wall towards opening 134 at a distal end of lumen 128, fluid (optionally provided by source 220) can flow through openings 34B and into lumen 128, thereby reducing the vacuum in lumen 128, thereby preventing damage to the intestinal wall.

Figure 9A:
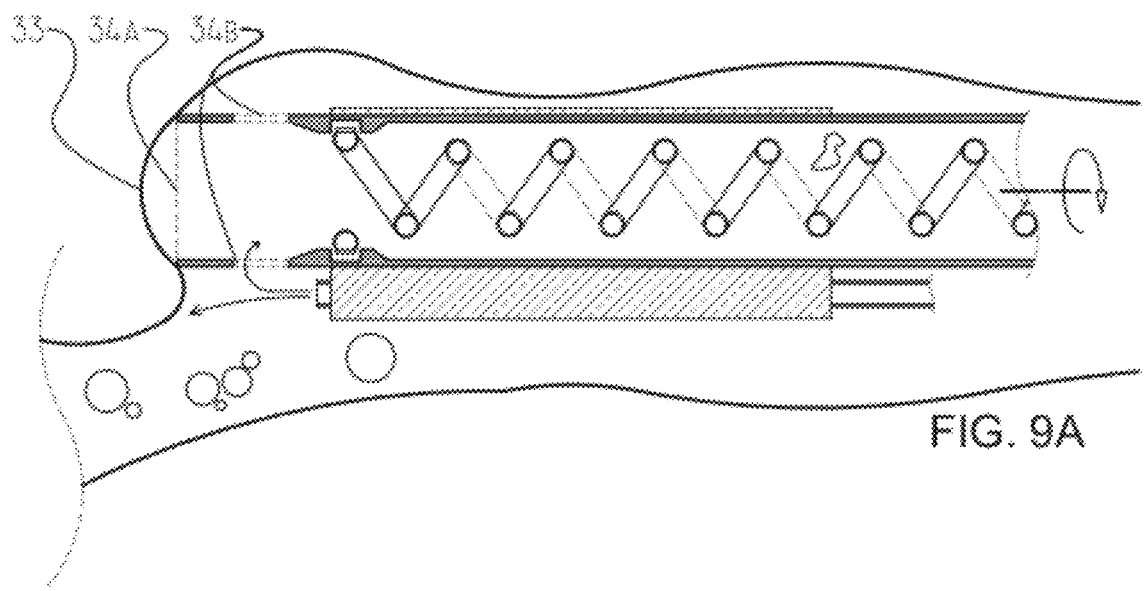
FIGS. 9A-9C present water jets being used to keep open a bypass orifice, according to some embodiments of the present invention.
Figure 9B:
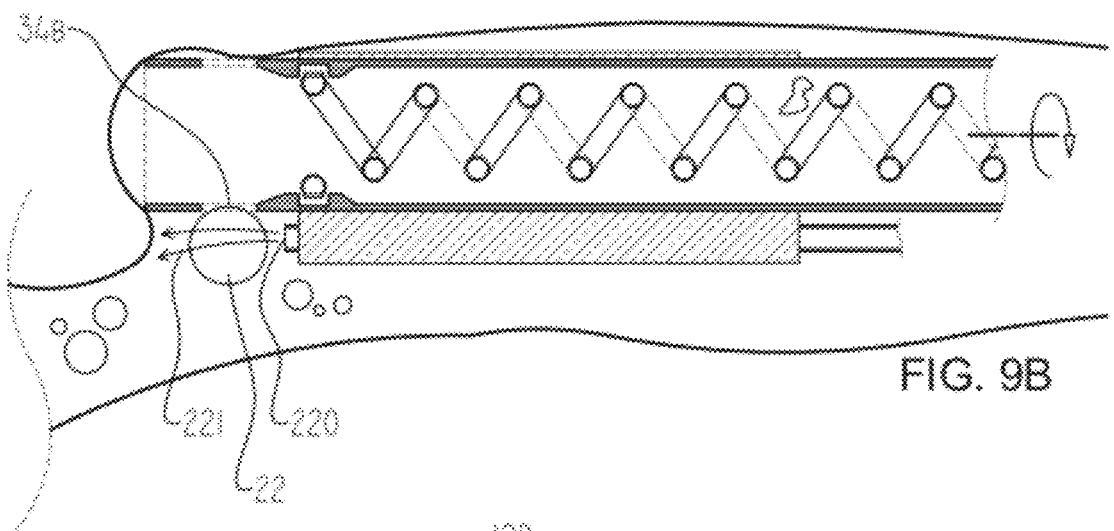
Figure 9C:
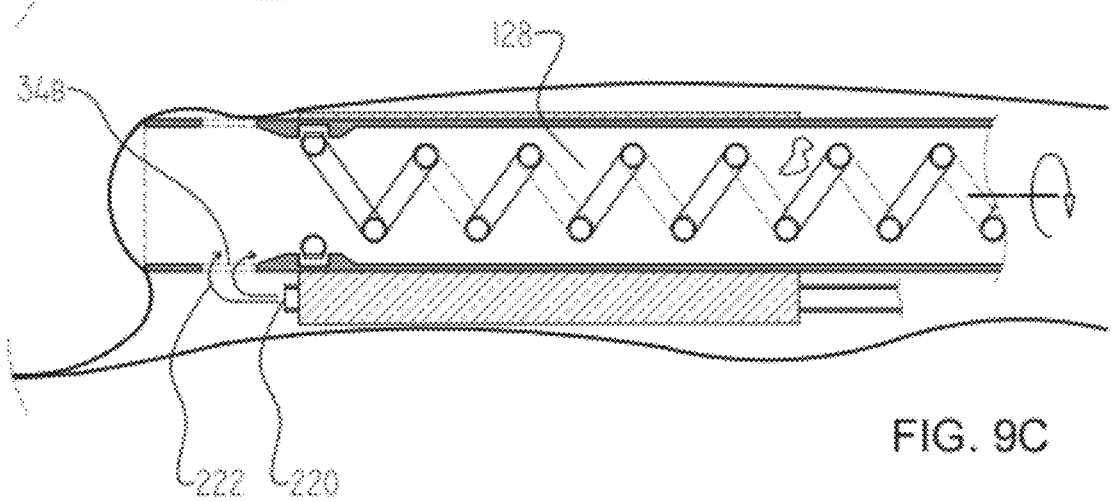

FIGS. 9A-9C present an additional advantage of embodiments where water source 220 is directed towards and across opening(s) 34B, according to embodiments of the present invention. It may be understood that if fluid is entering lumen 128 through an opening 34B because of a relative low pressure in lumen 128, it is not unlikely that pieces 22 of feces or other materials may be moved towards opening 34B and may block opening 34B. This situation is shown in FIG. 9B where a large piece of feces 22 has lodged in on opening 34B.

By positioning a water nozzle 220 near opening 34B and aiming jets 221 from that nozzle across opening 34B, this dangerous situation can be resolved, in that water jets 221 from nozzle 220 can be made strong enough to displace pieces 22 which block or which risk blocking opening 34B, as shown in FIG. 9B. FIG. 9C shows the situation after water jet 221 has successfully cleaned opening 34B, which is again open and available to prevent dangerous suction from developing in lumen 128.

An additional configuration enabling to provide fluid in an exhaust lumen when required to prevent excessively low pressure is presented by FIGS. 10A-10D, according to some embodiments of the present invention.

Figure 10A:
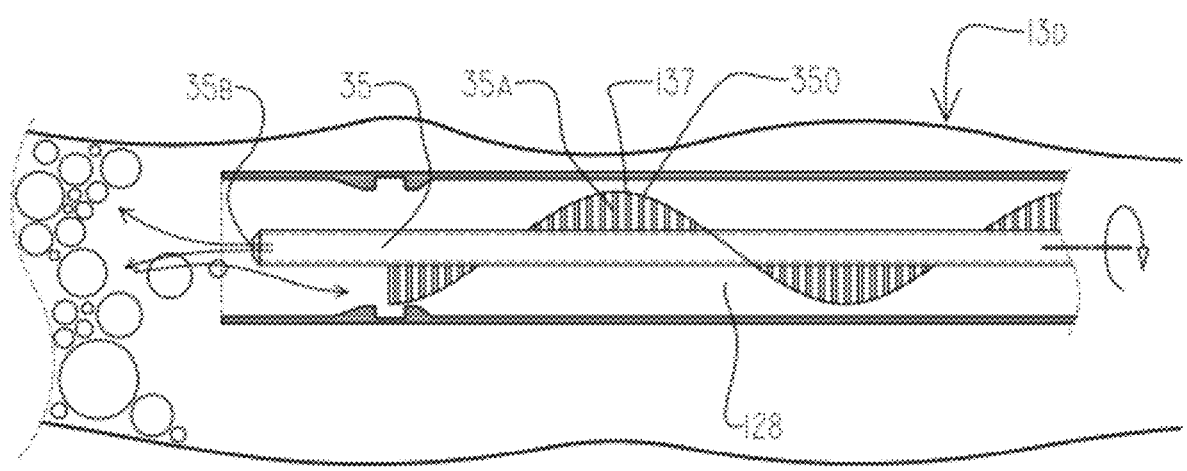
FIGS. 10A-10D present a helical matter transportation mechanism which comprises a hollow central portion, according to some embodiments of the present invention.

FIGS. 10A-10D present a helical matter transportation mechanism 137 which comprises a hollow central portion 35, according to embodiments of the present invention. Optionally, as shown in FIG. 10A, central portion 35 supports a helical structure 35A mounted on the exterior of a central cylinder 35. That helical structure may be a helical brush 350. Cylinder 35 may be rotated, thereby rotating helical structure 35A and enabling helical structure 35A to function as a matter transportation device 137.

Optionally, cylinder 35 is hollow and serves as a fluid input conduit. Optionally, hollow cylinder 35 comprises a nozzle 35B designed to deliver water or other fluid to an intestine near a distal end of cylinder 35.

Figure 10B:
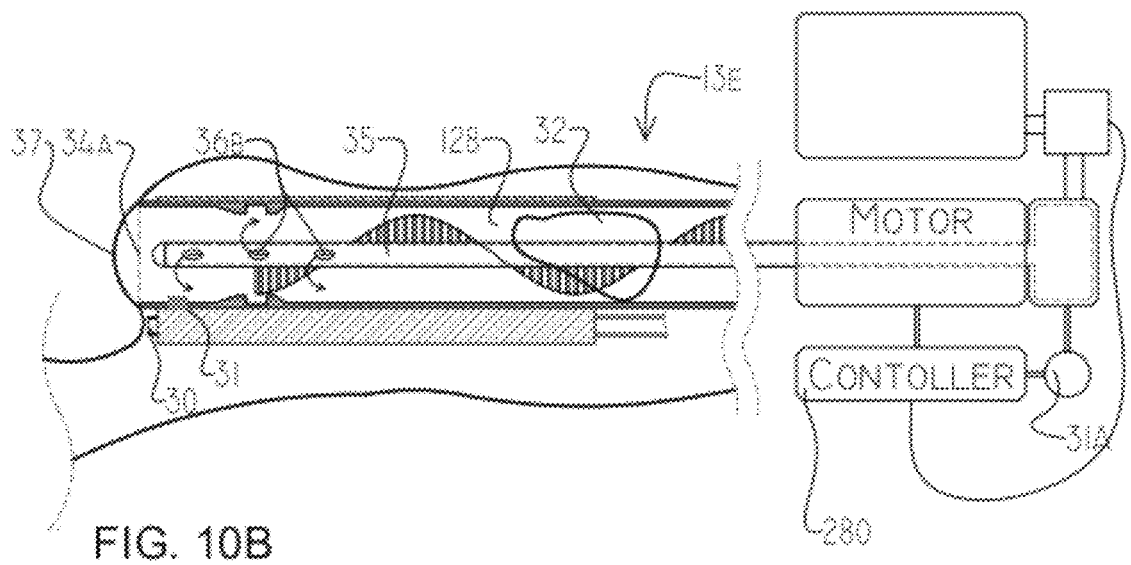

FIG. 10B presents a cleaning device 13E which differs from device 13D in that cylinder 35 comprises one or more bypass orifice(s) 36B. An interior lumen of cylinder 35 is connected to a fluid source. In the case that an excessive or dangerous vacuum develops within lumen 128 of device 13E, fluid such as water is enabled to pass from cylinder 35 into lumen 128 through opening(s) 36B, thereby raising pressure within lumen 128 and preventing dangerous levels of suction from developing within lumen 128.

Supply of water or other fluid through orifices 36B may be commanded by a controller in response to signals from a pressure sensor 31. Alternatively, orifices 36B may be provided with an automatic valve (e.g. a rubber flap) near orifices 36B or elsewhere within cylinder 35, enables fluid to flow from cylinder 35 into lumen 128 when a large pressure differential develops between the internal lumen of cylinder 35 and lumen 128, thereby reducing pressure within the evacuation conduit.

Figure 10C:
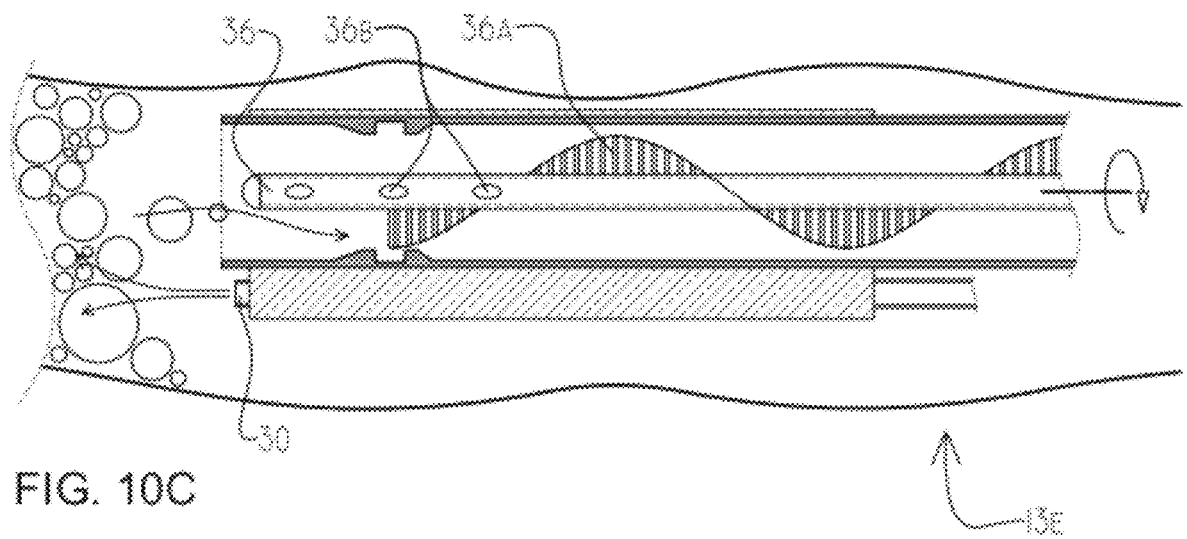
Figure 10D:
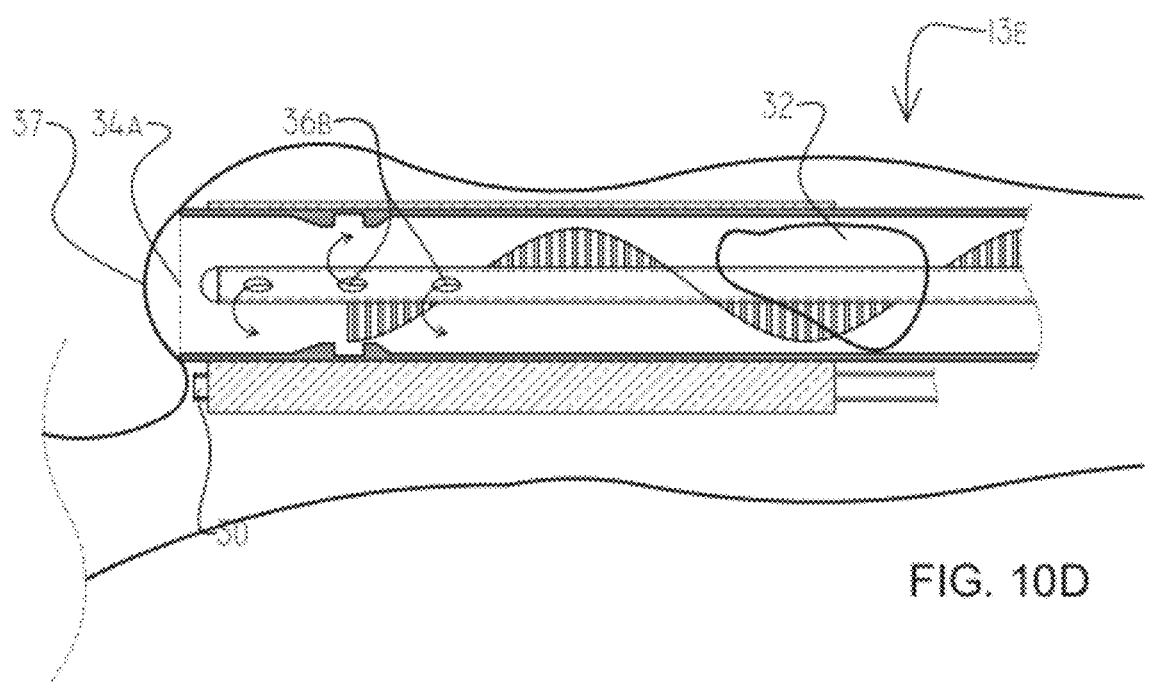

FIG. 10C shows device 13D functioning normally, with no fluid passing through orifices 36B, while FIG. 10D shows a situation in which a distal end of lumen 128 is blocked, movement of a large piece of feces 32 is causing suction in lumen 128, and fluid is being drawn from orifices 36B and is reducing that suction.

FIGS. 9A-9C presented what might be called an "external bypass", whereby fluid from the intestine may be drawn into an exhaust lumen 128 to reduce a vacuum therein. FIGS. 10A-10D presented what might be called an "internal bypass", where fluid from a dedicated source provides a fluid flow directly from that source into the interior of lumen 128 to reduce a vacuum therein.

Figure 11:
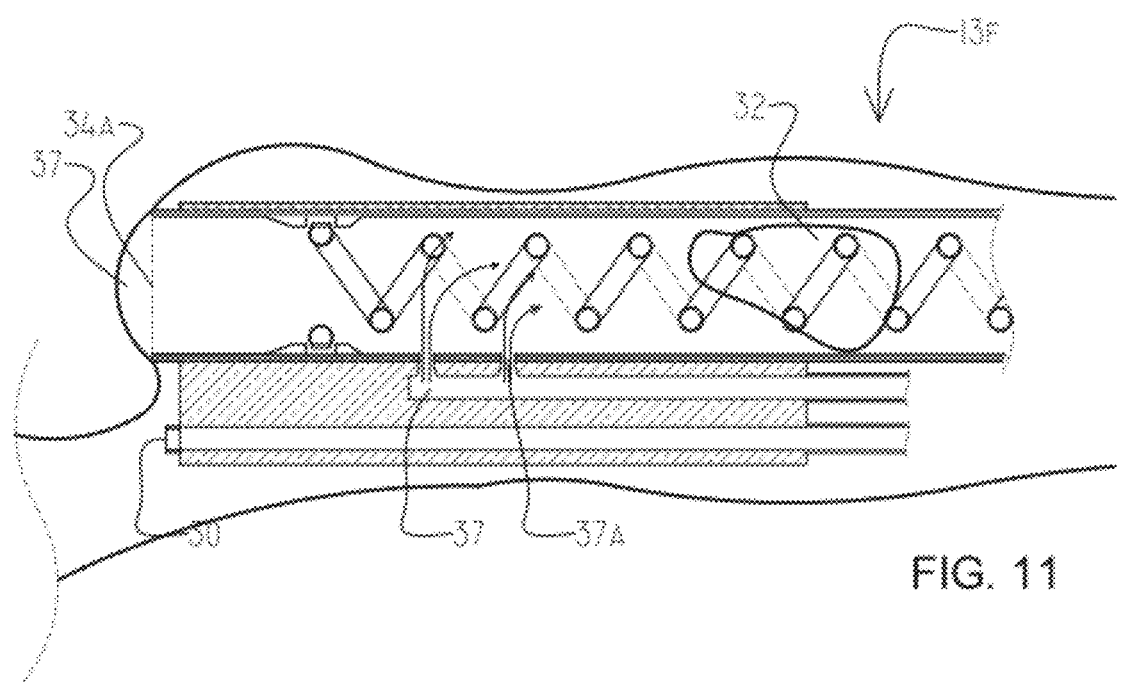
FIG. 11 presents an additional bypass configuration, according to some embodiments of the present invention.

Attention is now drawn to FIG. 11, which presents another configuration which comprises an internal bypass, according to an embodiment of the present invention. In a cleaner 13F shown in FIG. 11, a dedicated fluid supply channel 37 is used to provide fluid flow into a lumen 128 in case of dangerously low pressure therein. As noted above, control of such a flow can be by means of a controller responding to a sensor, or by means of a valve which opens when a pressure differential exceeds a predetermined amount value.

It is expected that during the life of a patent maturing from this application many relevant endoscopes will be developed, and the scope of the term "endoscope" is intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An intestinal cleaning device configured to supply liquid into a colon to grain fecal matter so that the resultant mixture of liquid and fecal matter can be evacuated, and constructed with or attachable to an endoscope or colonoscope, said device comprising:
   a fluid conduit comprising a nozzle at a distal end of the cleaning device and configured for delivery of the liquid by a fluid jet directed through the nozzle to grain fecal matter while the cleaning device is inserted to said intestine;
   an evacuation conduit configured to evacuate material grained by the fluid jet through an opening at said distal end of the cleaning device;
   a pressure sensor positioned within a lumen of said evacuation conduit and operable to measure pressure within said evacuation conduit;
   a controller configured to control delivery of said liquid and removal of matter via said evacuation conduit as a function of said measured pressure; and
   one or more openings positioned on said evacuation conduit, and configured to prevent a dangerously low pressure in said evacuation conduit by drawing enough fluid through said one or more openings to thereby raise said low pressure and prevent damage of a wall of said intestine.

2. The intestinal cleaning device as in claim 1, wherein said pressure sensor is active while said evacuation conduit is removing matter from said intestine.

3. The intestinal cleaning device as in claim 1, wherein said controller is configured to apply suction to said conduit to remove liquid from said intestine.

4. An intestinal cleaning system comprising:
   said intestinal cleaning device of claim 1; and
   the endoscope able to reach up to a cecum.

5. The intestinal cleaning device as in claim 1, wherein said openings are located on a lateral part of said evacuation conduit.

6. The intestinal cleaning device as in claim 1, wherein the fluid source comprises a fluid source external to said intestine, the conduit configured for delivery of fluid is in fluid communication with the external fluid source, and at least one of said openings is positioned near said fluid delivery conduit, so that fluid from said external fluid source can flow into said evacuation conduit.

7. The intestinal cleaning device as in claim 6, wherein said fluid delivery conduit is directed towards and across said at least one opening.

8. The intestinal cleaning device as in claim 7, wherein a jet of fluid from said fluid delivery conduit is made strong enough to displace pieces which block or risk blocking said at least one opening.

9. The intestinal cleaning device as in claim 1, wherein the evacuation conduit comprises a matter transportation mechanism to actively remove matter from said intestine; and wherein said matter transportation mechanism comprises a hollow central portion connected to a fluid source external to said intestine, and said one or more openings allow said external fluid to flow into said evacuation conduit.

10. The intestinal cleaning device as in claim 1, wherein said evacuation conduit comprises a dedicated fluid supply channel having said one or more openings allow fluid from said dedicated fluid supply to flow into said evacuation conduit.

11. The intestinal cleaning device as in claim 1, wherein said dangerously low pressure comprises a force strong enough to draw intestinal tissues into said evacuation conduit so that said intestinal tissues are damaged.

12. The intestinal cleaning device of claim 1, wherein the delivered fluid comprises gas.

13. An intestinal cleaning device according to claim 1, wherein the jets comprise high-pressure fluid supplied by said fluid conduit at a velocity between 0.1 m/s and 20 m/s rate to dismember waste solids in the intestine.

14. The intestinal cleaning device of claim 1, wherein an intake aperture of the evacuation conduit is larger than an exit aperture of the nozzle and is sized to allow intake of fecal pieces 0.5 cm in diameter.

15. The intestinal cleaning device of claim 1, wherein the evacuation conduit comprises a lumen with a longitudinal axis, and the opening at the distal end is oriented transversely across said axis and configured to press against an intestinal wall for evacuation of the liquid and fecal matter mixture upon insertion of the evacuation conduit into said intestine.

16. The intestinal cleaning device of claim 1, wherein the fluid drawn through the one or more openings is drawn from a fluid source.

17. An intestinal cleaning device comprising:
   an evacuation conduit which comprises a matter transportation mechanism to actively remove matter from said intestine by suction pressure, a lumen with a longitudinal axis, and a distal opening oriented transversely across said axis and configured to press against an intestinal wall for evacuation of a liquid and fecal matter mixture upon insertion of the evacuation conduit into said intestine;
   a pressure sensor positioned within said evacuation conduit, said pressure sensor positioned near the distal opening and configured to detect pressure in said evacuation conduit that is strong enough to damage tissue of said intestinal wall upon contact with said distal opening during said suction; and a controller configured to at least one of cease operation of said matter transport mechanism, reverse direction of said matter transport mechanism, and purge said evacuation conduit in response to a detected pressure in the evacuation conduit strong enough to damage said tissue of said intestinal wall.

18. The intestinal cleaning device as in claim 17, wherein said pressure sensor is positioned at a distal end of said evacuation conduit.

19. A method of cleaning a colon comprising:
  providing liquid into said colon to mix with, dilute, and partially dissolve fecal matter therein;
  removing, by suction, the resultant mixture of liquid and fecal matter from next to a wall of said colon and through a distal opening of an evacuation conduit;
  monitoring a pressure of a distal end of said evacuation conduit;
  sucking a portion of the wall into the distal opening;
  sensing a change in the monitored pressure due to blockage of the distal opening by the wall; and
  reducing the suction, based on the sensing.

20. The method according to claim 19, wherein said monitoring occurs during said providing and said removing.

21. The method according to claim 19, wherein the reducing the suction comprises at least one of stopping said removing, purging said evacuation conduit, and reversing direction of an active transport mechanism in said evacuation conduit.

22. The method according to claim 19, further comprising:
  providing an external fluid supply external to said colon;
  directing said external fluid supply into said evacuation conduit to increase said pressure.

23. The method according to claim 19, further comprising:
  cleaning up to a cecum while performing acts of said providing, said removing and said monitoring.

* * * * *

UNITED STATES PATENT AND TRADEMARK OFFICE
CERTIFICATE OF CORRECTION

PATENT NO. : 10,512,718 B2
APPLICATION NO. : 13/557363
DATED : December 24, 2019
INVENTOR(S) : Boris Shtul et al.

It is certified that error appears in the above-identified patent and that said Letters Patent is hereby corrected as shown below:

On the Title Page

Item (73) Assignee, Line 2, "(IN)" should be changed to -- (IL) --

Signed and Sealed this
Seventeenth Day of March, 2020

Andrei Iancu
*Director of the United States Patent and Trademark Office*